United States Patent
Vega et al.

(10) Patent No.: US 12,071,431 B2
(45) Date of Patent: Aug. 27, 2024

(54) PYRIDIN-SULFONAMIDE COMPOUNDS FOR THE TREATMENT OF CONDITIONS RELATED TO INTERLEUKIN 1 BETA

(71) Applicant: ALLINKY BIOPHARMA, Madrid (ES)

(72) Inventors: Miguel Vega, Madrid (ES); Esther Carrasco, Madrid (ES); Patricia Gómez, Madrid (ES); Pedro Campos, Madrid (ES); Juan Gómez-Reino, Madrid (ES); Juan Jesús Pérez, Madrid (ES); Ángel Messeguer, Madrid (ES)

(73) Assignee: ALLINKY BIOPHARMA, Madrid (ES)

( * ) Notice: Subject to any disclaimer, the term of this patent is extended or adjusted under 35 U.S.C. 154(b) by 642 days.

(21) Appl. No.: 17/293,877

(22) PCT Filed: Nov. 14, 2019

(86) PCT No.: PCT/EP2019/081410
§ 371 (c)(1),
(2) Date: May 13, 2021

(87) PCT Pub. No.: WO2020/099603
PCT Pub. Date: May 22, 2020

(65) Prior Publication Data
US 2022/0002276 A1    Jan. 6, 2022

(30) Foreign Application Priority Data

Nov. 14, 2018   (EP) ..................... 18380017

(51) Int. Cl.
| | | |
|---|---|---|
| *C07D 405/14* | (2006.01) | |
| *A61P 1/16* | (2006.01) | |
| *C07D 213/70* | (2006.01) | |
| *C07D 401/04* | (2006.01) | |
| *C07D 401/14* | (2006.01) | |

(52) U.S. Cl.
CPC ............. *C07D 405/14* (2013.01); *A61P 1/16* (2018.01); *C07D 213/70* (2013.01); *C07D 401/04* (2013.01); *C07D 401/14* (2013.01)

(58) Field of Classification Search
CPC ............. A61K 31/4545; C07D 213/70; C07D 401/04; C07D 401/14; C07D 405/04; C07D 405/14; A61P 1/16; A61P 11/00; A61P 29/00; A61P 9/00
See application file for complete search history.

(56) References Cited

U.S. PATENT DOCUMENTS

2020/0369671 A1   11/2020   Garcia et al.

FOREIGN PATENT DOCUMENTS

| WO | 2008/024284 A2 | 2/2008 |
| WO | 2008/091863 A1 | 7/2008 |
| WO | WO2018183145 | * 10/2018 |

OTHER PUBLICATIONS

Barlo et al., "Genetic variability in the ILIRN gene and the balance between interleukin (IL)-1β receptor agonist and IL-1β in idiopathic pulmonary fibrosis," *Clinical and Experimental Immunology* 346-351, 2011.
Burgy et al., "Pleural inhibition of the caspase-1/IL-1β pathway diminishes profibrotic lung toxicity of bleomycin," *Respiratory Research* 17(162):1-10, 2016.
Dowman et al., "Pathogenesis of non-alcoholic fatty liver disease," *Q J Med* 103:71-83, 2010.
Gressner et al., "Non-invasive biomarkers for monitoring the fibrogenic process in liver: A short survey," *World J Gastroenterol* 15(20):2433-2440, 2009.
Hansen et al., "Mouse models of nonalcoholic steatohepatitis in preclinical drug development," *Drug Discovery Today* 22(11):1707-1718, 2017.
Hoshino et al., "Role of Proinflammatory Cytokines IL-18 and IL-1β in Bleomycin-Induced Lung Injury in Humans and Mice," *American Journal of Respiratory Cell and Molecular Biology* 41:661-670, 2009.
Kodama et al., "c-Jun N-terminal Kinase-1 From Hematopoietic Cells Mediates Progression From Hepatic Steatosis to Steatohepatitis and Fibrosis in Mice," *Gastroenterology* 137(4):1467-1477, 2009.
Rosenthal et al., "Potent and Selective Small Molecule Inhibitors of Specific Isoforms of Cdc2-like Kinases (Clk) and Dual Specificity Tyrosine-Phosphorylation-Regulated Kinases (Dyrk)," 21(10):3152-3158, 2011.
Schulien et al., "The transcription factor c-Jun/AP-1 promotes liver fibrosis during non-alcoholic steatohepatitis by regulating Osteopontin expression," *Cell Death & Differentiation* 26:1688-1699, 2019.
Vuppalanchi et al., "Nonalcoholic Fatty Liver Disease and Nonalcoholic Steatohepatitis: Selected Practical Issues in Their Evaluation and Management," *Hepatology* 49: 306-317, 2009.

* cited by examiner

Primary Examiner — Umamaheswari Ramachandran
(74) Attorney, Agent, or Firm — SEED INTELLECTUAL PROPERTY LAW GROUP LLP

(57) ABSTRACT

The present invention relates to a novel class of pyridine-sulfonamide compounds and to compositions comprising the same. The compounds and compositions are useful as medicaments in the treatment of diseases responsive to inhibition of IL-1β, such as non-alcoholic steatohepatitis (NASH) and idiopathic pulmonary fibrosis (IPF).

15 Claims, 7 Drawing Sheets

PYRIDIN-SULFONAMIDE COMPOUNDS FOR THE TREATMENT OF CONDITIONS RELATED TO INTERLEUKIN 1 BETA

FIELD OF THE INVENTION

The present invention relates to a novel class of pyridine-sulfonamide compounds and to compositions comprising the same. The compounds and compositions (such as pharmaceutical compositions) of the present invention can be used as medicaments in the treatment of diseases related to interleukin 1 beta (IL-1β) such as inflammatory and fibrotic diseases.

BACKGROUND OF THE INVENTION

IL-1 has been shown to be involved in a wide range of human pathologies ranging from autoinflammatory diseases to rheumatoid arthritis, IL-1-blocking agents (IL-1Ra, Anakinra; anti-IL-1b monoclonal antibody [mAb], Canakinumab; and anti-IL-1a, MABp1) have been approved for clinical use or are being evaluated in some of these disorders (Dinarello, 2009; Gabay et al., 2010; Garlanda et al., 2013; Udalova et al., 2016).

IL-1 has long been associated with inflammation and innate immunity. It is now apparent that this cytokine plays differential roles in shaping and orienting innate immunity and inflammation in response to different microbial or environmental challenges. Moreover, during the last decade the preclinical research on the role of IL-1 beta (IL-1β) has extended beyond classic inflammation to understand its role in immunopathology, fibrotic disease, degenerative disease, cardiovascular disease and cancer. Additionally, clinical studies on the effect of blocking IL-1β(Aaron et al., 2018; Trankle C R et al., 2018; Ridker P M., 2018; Ridker P M., 2017) showed in over 10,000 patients that blocking IL-1 protected not only against atherosclerosis-driven cardiovascular mortality but also against a range of diseases including lung cancer, osteoarthritis, and gout. This finding, revealing of the diversity and yet commonality of disease mechanisms, suggests that IL-1 represents a paradigm for inflammation and immunity as well as a promising drug target (Montovani et al, 2019).

The production and subsequent secretion of IL-1β depends mainly on the activation of the toll-like receptor 4 (TLR4) and the inflammasome. In a first step, an inflammatory stimuli or an infection, signaling through the TLR4 receptor, triggers pro-IL-1β production; in a second step the inflammasome-activated caspase-1 proteolytically releases IL-1β into the bloodstream. This cytokine is responsible for the activation of T cells as well as antigen recognition, among other important functions. Interestingly the production of IL-1β depends on the action of mitogen-activated protein kinase (MAPK), a group of proteins within the signaling route of TLR4 receptors. MAPK such as p38, JNK and ERK activate nuclear factors that bind to gene promoters related to the production of IL-1β.

Thus, the inhibition of MAPK is a valid approach to avoid production of IL-1β in the context of inflammatory diseases and conditions.

Among inflammatory diseases and conditions driven by IL-1β the Non-alcoholic Steatohepatitis (NASH) and the Idiopathic Pulmonary Fibrosis (IPF) are of great importance. These diseases are unmet clinical needs with just a few therapeutic approaches mainly focused on symptomatic treatment.

Non-Alcoholic Steatohepatitis (NASH)

In particular, non-alcoholic fatty liver disease (NAFLD) is a common hepatic disorder with histological features of alcohol-induced fatty liver disease in individuals who consume little or no alcohol (Yeh M et al., 2007; Marchesini G et al., 2003). NAFLD is due to the abnormal retention of lipids within cells (commonly defined as steatosis), an event more frequent in liver since this organ is primarily responsible of lipid metabolism. NAFLD has a spectrum of histological forms including hepatic steatosis, and non-alcoholic steatohepatitis (NASH), which is characterized by liver inflammation, steatosis, necrosis and fibrosis due to the disruption of liver cells.

Hepatic imaging systems are useful to evaluate also liver structure and presence of steatosis. However, liver biopsy remains the gold standard for evaluating liver fibrosis, but this method of analysis could not be done for every single study due to its invasiveness. Non-invasive evaluation of liver biochemistry and metabolism is often used to define liver diseases, such as in NAFLD and NASH (Gressner A et al., 2009, World J Gastroenterol; 15: 2433-2440; Vuppalanchi R and Calacanis N, 2009, Hepatology; 49: 306-317). By using plasma, high level of enzymes such as Alanine aminotransferase (ALAT), Aspartate aminotransfersase (ASAT), Alkaline Phosphatase (AP), and/or Gamma Glutamyl Transpeptidase (GGT), as well as the presence of other proteins of liver origin (including haptoglobin, total bilirubin, alpha-2-microglobulin, Resistin, cleaved or intact cytokeratin-18) are commonly measured in addition to serum glucose and insulin resistance parameters.

Means for an effective treatment for liver fibrotic diseases, and NAFLD and NASH in particular, are still insufficient. No treatment is established for patients with NASH, and several therapeutic options are tested in clinical trial (Vuppalanchi R and Chalasani N, 2009, Hepatology; 49: 306-317; Dowman J. K et al., 2009, Q J Med; 103: 71-83). These studies involve the use of many different families of chemical compounds (fibrates, thiazolidinediones, biguanides, statins, cannabinoids) and therapeutic targets (nuclear receptors, angiotensin receptors, cannabinoid receptors, HMG-CoA reductase).

It has been shown that c-Jun expression correlates with disease progression from steatosis to NASH (Schulien et al, 2019, Cell Death & Differentiation; 26; 1688-1699). It has also been shown that JNK1 knockout mice are resistant to diet-induced steatohepatitis and liver fibrosis and that JNK1 contributes to the development of liver fibrosis by inducing chronic inflammation (Kodama et al., 2009, Gastroenterology; 137(4); 1467-1477).

Murine animal models have been developed as preclinical in vivo models for NASH (Hansen H et al., 2017, Drug Discovery Today, 22: 1707-1718). C57BL/6 mice are the most frequently used as it is sensitive to a high-fat diet and develops many of the same symptoms observed in human NASH. It is furthermore known that injection of streptozotocin sensitizes mice models to high-fat diets in developing NASH.

Idiopathic Pulmonary Fibrosis (IPF)

Idiopathic pulmonary fibrosis (IPF) is an interstitial lung disease characterised by chronic inflammation and subsequent progressive scarring of the lungs. The interstitial lung diseases (ILDs) are a heterogeneous group of parenchymal lung diseases characterised by varying degrees of inflammation and fibrosis. Some of these may occur secondary to a known precipitant such as drugs, autoimmune connective tissue disease, hypersensitivity to inhaled organic antigens, or sarcoidosis, whilst others, the idiopathic interstitial pneumonias (IIPs), have no identifiable cause. Idiopathic pulmonary fibrosis (IPF) is one of the most aggressive forms of IIP, characterised by chronic, progressive fibrosis associated with inexorable decline in lung function, progressive respiratory failure, and high mortality (Shaney et al., 2018).

Over recent years, two novel antifibrotic therapies, pirfenidone and nintedanib, have been developed, providing treatment for many patients with IPF. Unfortunately, their profile as disease modifiers is poor and new therapeutics are needed.

Elevated levels of IL-1β are known to contribute to proinflammatory and pro-fibrotic environment in lungs of patients suffering from idiopathic pulmonary fibrosis (IPF) (Barlo et al., 2011) In preclinical research, animal models of lung fibrosis showed that transient expression of IL-1β induces acute lung injury and chronic repair leading to pulmonary fibrosis (Kolb M., 2001; Gasse P et al., 2011).

Moreover, the bleomycin-induced lung injury model of IPF has extensively demonstrated the role of IL-1β in lung fibrosis (Hoshino et al., 2009; Burgy et al., 2016).

The role of MAPK in IPF has also been the focus of animal and human studies, concluding that activated MAPKs are significantly increased in lung homogenates from patients with IPF compared with controls (Yoshida et al., 2002). Moreover, JNK inhibition reduces lung remodelling and pulmonary fibrotic systemic markers in animal models of IPF (Van del Velden J L et al., 2016). The research results in IPF point at activated MAPK, and subsequent production of IL-1β, as one of the main drivers for IPF onset and progression.

The need for novel therapeutic options for the management of liver disorders and other fibrotic disorders, in particular those involving liver and lung fibrosis, is still clear and urgent.

SUMMARY OF THE INVENTION

The present invention provides a novel class of compounds having Formula I and/or Formula Ia, which includes pharmaceutically acceptable salts thereof. The compounds of the invention are intended for the treatment of diseases responsive to inhibition of IL-1β such as non-alcoholic steatohepatitis (NASH) and idiopathic pulmonary fibrosis (IPF).

The compounds of the present invention are compounds of Formula I or pharmaceutically acceptable salts thereof:

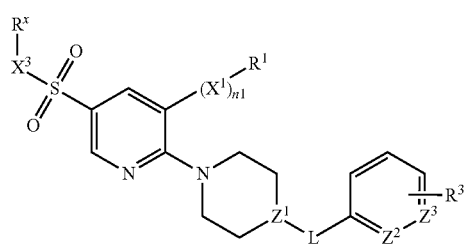

Formula I wherein
$R^1$ is an aromatic or heteroaromatic ring system optionally substituted with one or two substituents selected from the group consisting of $C_{1-4}$ alkyl-$Y^1$—, $C_{2-4}$ alkenyl-$Y^1$—, $C_{2-4}$ alkynyl-$Y^1$—, $C_{1-4}$ alkyl-$Y^1$— substituted with halo, such as fluoro, $C_{2-4}$ alkenyl-$Y^1$— substituted with halo, $C_{2-4}$ alkynyl-$Y^1$ substituted with halo, HO—$C_{1-4}$ alkanediyl-$Y^1$—, HO—$C_{2-4}$ alkenediyl-$Y^1$—, HO—$C_{2-4}$ alkynediyl-$Y^1$—, HO—$C_{1-4}$ alkanediyl-, HO—$C_{2-4}$ alkenediyl-, HO—$C_{2-4}$ alkynediyl-, $C_{1-4}$ alkyl-$C_{2-4}$ alkenyl-, $C_{2-4}$ alkynyl-, $C_{1-4}$ alkyl substituted with halo, $C_{2-4}$ alkenyl-substituted with halo, $C_{2-4}$ alkynyl-substituted with halo, and halogen; $Y^1$ is selected from the group consisting of O, S, NH, C(O), C(O)O, C(O)NH, O(CO) and NHC(O);
$X^1$ is NH, O, or $CH_2$;
n1 is 0 or 1;
$X^3$ is absent or $NR^y$;
$R^x$ and $R^y$ are independently $C_{1-4}$ alkyl, $C_{2-4}$ alkenyl, $C_{2-4}$ alkynyl, or H, such as $CH_3$ or H;
L is O, S, S(O), $S(O)_2$, NH, C(O), or $CH_2$;
$Z^1$, $Z^2$, and $Z^3$ are independently selected from N and CH;
$R^3$ is selected from the group consisting of H, halo, $C(O)NR^{2a}R^{2b}$, $C(O)OR^{2a}$, $OR^{2a}$, $NR^{2a}R^{2b}$, $OC(O)R^{2a}$, $NR^{2a}C(O)R^{2b}$, $C_{1-4}$ alkyl optionally substituted with one or more halo, $C_{2-4}$ alkenyl optionally substituted with one or more halo, and $C_{2-4}$ alkynyl optionally substituted with one or more halo, wherein $R^{2a}$ and $R^{2b}$ are independently selected from the group consisting of H, $C_{1-4}$ alkyl, $C_{2-4}$ alkenyl, and $C_{2-4}$ alkynyl.

In a further aspect, the present invention concerns a pharmaceutical composition comprising a compound according to the present invention and a pharmaceutically acceptable excipient or carrier.

In another aspect, the present invention concerns the compound according to the present invention or the composition according to the present invention for use as a medicament.

In still a further aspect, the present invention concerns the compound according to the present invention or the composition according to the present invention for use in the treatment of diseases responsive to inhibition of IL-1β, such as non-alcoholic steatohepatitis (NASH) and idiopathic pulmonary fibrosis (IPF).

DETAILED DESCRIPTION OF THE INVENTION

Definitions

Figure 1:
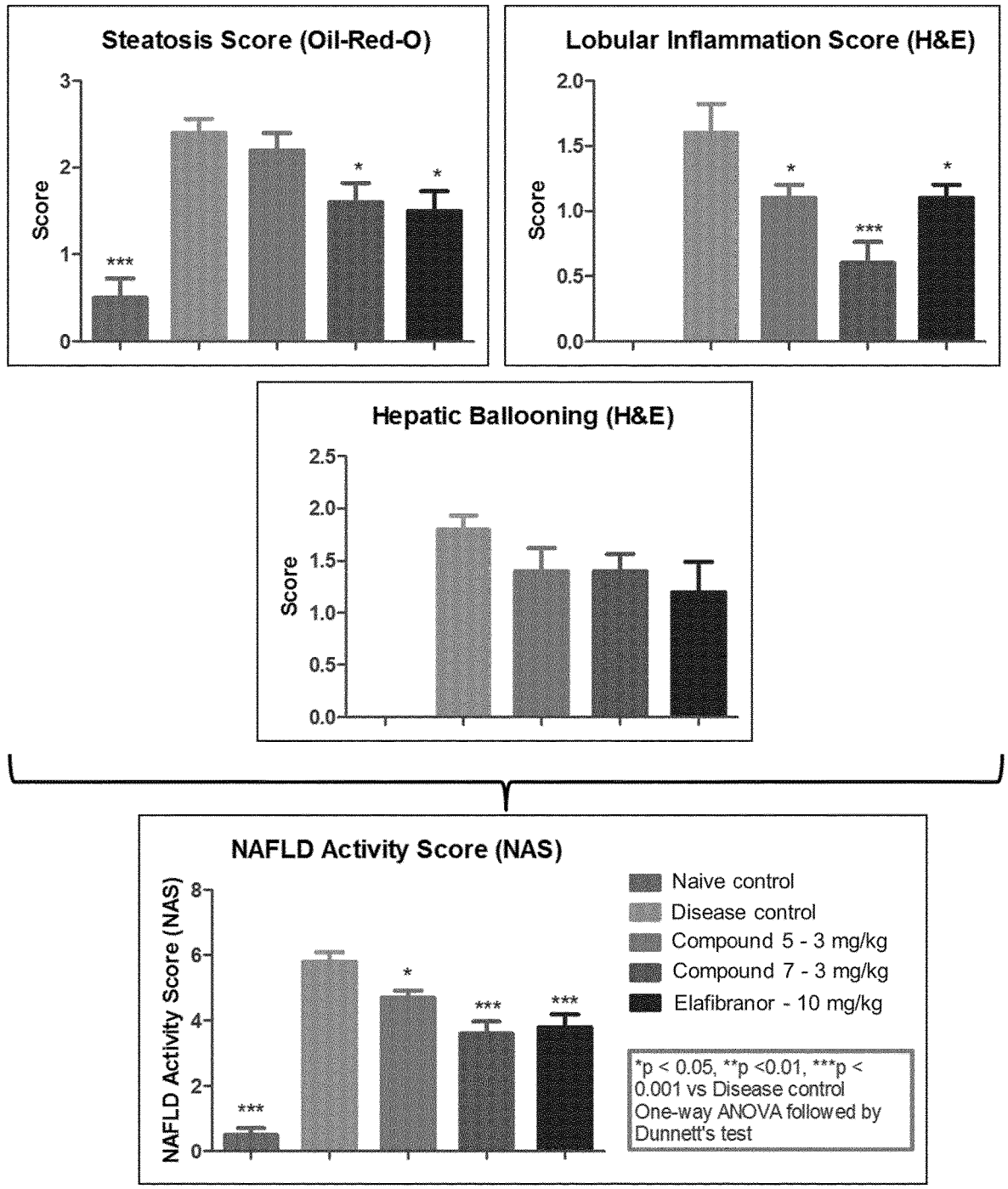
FIG. 1. Effect of Compound 5 and Compound 7 on NAFLD activity score (NAS).

In the present context, the term "$C_{1-4}$ alkyl" is intended to mean a linear or branched hydrocarbon group having 1 to 4 carbon atoms, such as methyl, ethyl, n-propyl, iso-propyl, n-butyl, iso-butyl, sec-butyl, and tert-butyl.

Similarly, the term "$C_{2-4}$ alkenyl" is intended to cover linear or branched hydrocarbon groups having 2 to 4 carbon atoms and comprising a double bond. Examples of alkenyl groups are vinyl, allyl, and butenyl. Preferred examples of alkenyl are vinyl and allyl, especially allyl.

In the present context the term "C$_{2-4}$ alkynyl" is intended to mean a linear or branched hydrocarbon group having 2 to 4 carbon atoms and containing a triple bond. Illustrative examples of C$_{2-4}$ alkynyl groups include acetylene, propynyl, butynyl, as well as branched forms of these. The position of unsaturation (the triple bond) may be at any position along the carbon chain. More than one bond may be unsaturated such that the "C$_{2-4}$ alkynyl" is a di-yne as is known to the person skilled in the art.

Herein, the term "halo" or "halogen" includes fluoro, chloro, bromo, and iodo, more particularly, fluoro, chloro and bromo.

In the present context the term "aromatic ring or ring system" is intended to mean a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl.

The term "heteroaromatic ring or ring system" is intended to mean a fully or partially aromatic carbocyclic ring or ring system where one or more of the carbon atoms have been replaced with heteroatoms, e.g. nitrogen (=N— or —NH—), sulphur, and/or oxygen atoms. Examples of such heteroaromatic ring or ring system groups are oxazolyl, isoxazolyl, thiazolyl, isothiazolyl, pyrrolyl, imidazolyl, pyrazolyl, pyridinyl, pyrimidinyl, pyrazinyl, pyridazinyl, triazinyl, coumaryl, furyl, thienyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl, phenoxazonyl, benzofuranyl, dihydrobenzofuranyl and benzodioxolyl.

In the present context, the term "heterocyclic ring or ring system" is intended to mean a non-aromatic carbocyclic ring or ring system where one or more of the carbon atoms have been replaced with heteroatoms, e.g. nitrogen (=N— or —NH—), sulphur, and/or oxygen atoms. Examples of such heterocyclic groups are imidazolidine, piperazine, hexahydropyridazine, hexahydropyrimidine, diazepane, diazocane, pyrrolidine, piperidine, azepane, azocane, aziridine, azirine, azetidine, pyroline, tropane, oxazinane (morpholine), azepine, dihydroazepine, tetrahydroazepine, hexahydroazepine, oxazolane, oxazepane, oxazocane, thiazolane, thiazinane, thiazepane, thiazocane, oxazetane, diazetane, thiazetane, tetrahydrofuran, tetrahydropyran, oxepane, tetrahydrothiophene, tetrahydrothiopyrane, thiepane, dithiane, dithiepane, dioxane, dioxepane, oxathiane and oxathiepane.

In the present context, the term "optionally substituted" is intended to mean that the group in question may be substituted one or more times, preferably 1-2 times. Furthermore, the term "optionally substituted" may also mean that the group in question is unsubstituted.

The compounds of the present invention can be in a free form or in the form of a pharmaceutically acceptable salt. In the context of the present invention, the term "pharmaceutically acceptable salt" is to be understood as a salt formed with either a base or an acid, wherein the resulting counterion does not significantly add to the toxicity of the compound of the present invention.

Examples of pharmaceutically acceptable salts include inorganic acid salts such as hydrochloride, sulfate, nitrate, phosphate or hydrobromide, etc., organic acid salts such as acetate, fumarate, oxalate, citrate, methanesulfonate, benzenesulfonate, p-toluenesulfonate or maleate, etc. Also, when the compound has a substituent such as carboxyl group, there may be mentioned a salt with a base (for example, alkali metal salt such as sodium salt, potassium salt, etc. or alkaline earth metal salt such as calcium salt, etc.).

Compounds

The compounds of the invention are compounds of Formula I or pharmaceutically acceptable salts thereof:

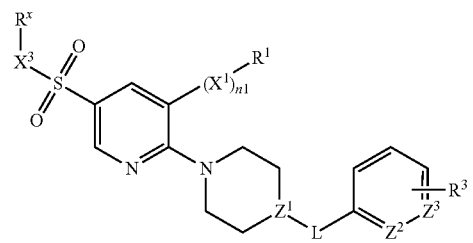

Formula I wherein

R$^1$ is an aromatic or heteroaromatic ring system optionally substituted with one or two substituents selected from the group consisting of C$_{1-4}$ alkyl-Y$^1$—, C$_{2-4}$ alkenyl-Y$^1$—, C$_{2-4}$ alkynyl-Y$^1$—, C$_{1-4}$ alkyl-Y$^1$— substituted with halo, such as fluoro, C$_{2-4}$ alkenyl-Y$^1$— substituted with halo, C$_{2-4}$ alkynyl-Y$^1$ substituted with halo, HO—C$_{1-4}$ alkanediyl-Y$^1$—, HO—C$_{2-4}$ alkenediyl-Y$^1$—, HO—C$_{2-4}$ alkynediyl-Y$^1$—, HO—C$_{1-4}$ alkanediyl-, HO—C$_{2-4}$ alkenediyl-, HO—C$_{2-4}$ alkynediyl-, C$_{1-4}$ alkyl-C$_{2-4}$ alkenyl-, C$_{2-4}$ alkynyl-, C$_{1-4}$ alkyl substituted with halo, C$_{2-4}$ alkenyl-substituted with halo, C$_{2-4}$ alkynyl-substituted with halo, and halogen;

Y$^1$ is selected from the group consisting of O, S, NH, C(O), C(O)O, C(O)NH, O(CO) and NHC(O);

X$^1$ is NH, O, or CH$_2$;

n1 is 0 or 1;

X$^3$ is absent or NR$^y$;

R$^x$ and R$^y$ are independently C$_{1-4}$ alkyl, C$_{2-4}$ alkenyl, C$_{2-4}$ alkynyl, or H, such as CH$_3$ or H;

L is O, S, S(O), S(O)$_2$, NH, C(O), or CH$_2$;

Z$^1$, Z$^2$, and Z$^3$ are independently selected from N and CH;

R$^3$ is selected from the group consisting of H, halo, C(O)NR$^{2a}$R$^{2b}$, C(O)OR$^{2a}$, OR$^{2a}$, NR$^{2a}$R$^{2b}$, OC(O)R$^{2a}$, NR$^{2a}$C(O)R$^{2b}$, C$_{1-4}$ alkyl optionally substituted with one or more halo, C$_{2-4}$ alkenyl optionally substituted with one or more halo, and C$_{2-4}$ alkynyl optionally substituted with one or more halo, wherein R$^{2a}$ and R$^{2b}$ are independently selected from the group consisting of H, C$_{1-4}$ alkyl, C$_{2-4}$ alkenyl, and C$_{2-4}$ alkynyl.

In one embodiment, the compound of formula I is a compound having the formula Ia:

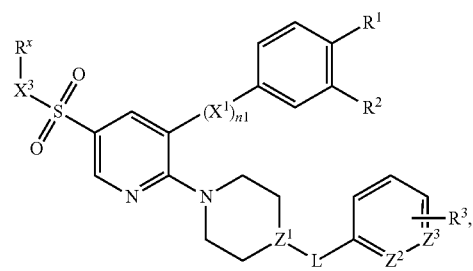

wherein

R$^1$ is selected from the group consisting of C$_{1-4}$ alkyl-Y$^1$—, C$_{2-4}$ alkenyl-Y$^1$—, C$_{2-4}$ alkynyl-Y$^1$—, C$_{1-4}$ alkyl-Y$^1$— substituted with halo, such as fluoro, C$_{2-4}$ alkenyl-$Y^1$-substituted with halo, $C_{2-4}$ alkynyl-$Y^1$ substituted with halo, HO—$C_{1-4}$ alkanediyl-$Y^1$—, HO—$C_{2-4}$ alkenediyl-$Y^1$—, HO—$C_{2-4}$ alkynediyl-$Y^1$—, HO—$C_{1-4}$ alkanediyl-, HO—$C_{2-4}$ alkenediyl-, HO—$C_{2-4}$ alkynediyl-, $C_{1-4}$ alkyl-$C_{2-4}$ alkenyl-, $C_{2-4}$ alkynyl-, $C_{1-4}$ alkyl substituted with halo, $C_{2-4}$ alkenyl-substituted with halo, $C_{2-4}$ alkynyl-substituted with halo, and halogen;

$R^2$ is hydrogen; or $R^1$ together with $R^2$ forms an aromatic, heteroaromatic, cyclic or heterocyclic five- or six-membered ring optionally substituted with one or two substituents selected from the group consisting of $C_{1-4}$ alkyl-$Y^1$—, $C_{2-4}$ alkenyl-$Y^1$—, $C_{2-4}$ alkynyl-$Y^1$—, $C_{1-4}$ alkyl-$Y^1$— substituted with halo, such as fluoro, $C_{2-4}$ alkenyl-$Y^1$— substituted with halo, $C_{2-4}$ alkynyl-$Y^1$ substituted with halo, HO—$C_{1-4}$ alkanediyl-, HO—$C_{2-4}$ alkenediyl-, HO—$C_{2-4}$ alkynediyl-, $C_{1-4}$ alkyl-$C_{2-4}$ alkenyl-, $C_{2-4}$ alkynyl-, $C_{1-4}$ alkyl substituted with halo, $C_{2-4}$ alkenyl-substituted with halo, $C_{2-4}$ alkynyl-substituted with halo, and halogen; and $X^1$, n1, $Y^1$, $X^3$, $R^x$, $R^y$, L, $Z^1$, $Z^2$, $Z^3$, $R^3$ are as defined for the compound of formula I.

In a further embodiment, in the compounds of formula I and formula Ia, $X^3$ is $NR^y$, giving rise to the compounds of formula II and IIa:

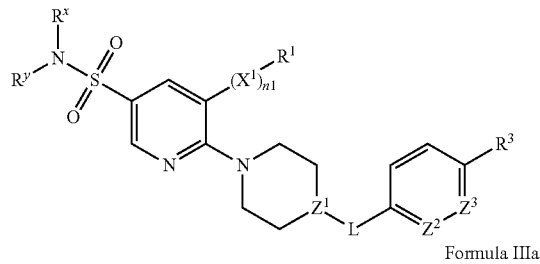

$X^1$, n1, $Y^1$, $R^x$, $R^y$, L, $Z^1$, $Z^2$, $Z^3$, $R^1$, $R^2$, $R^3$ are as defined for the compounds of formula I and formula Ia.

In still a further embodiment, in the compounds of formula II and formula IIa, $R^3$ is in the para position, giving rise to the compounds of formula III and IIIa:

$X^1$, n1, $Y^1$, $R^x$, $R^y$, L, $Z^1$, $Z^2$, $Z^3$, $R^1$, $R^2$, $R^3$ are as defined for the compounds of formula I and formula Ia.

In yet a further embodiment, in the compounds of formula III and formula IIIa, $Z^2$ is CH, giving rise to the compounds of formula IV and IVa:

$X^1$, n1, $Y^1$, $R^x$, $R^y$, L, $Z^1$, $Z^3$, $R^1$, $R^2$, $R^3$ are as defined for the compounds of formula I and formula Ia.

In one embodiment of the compounds according to the invention, $Y^1$ is selected from the group consisting of O, S, NH, C(O), and C(O)NH. In a further embodiment, $Y^1$ is selected from the group consisting of O, S, and NH. In yet a further embodiment, $Y^1$ is O.

In another embodiment of the compounds according to the invention, $X^1$ is NH or O. In yet another embodiment, $X^1$ is NH or O and n1 is 1.

In a further embodiment of the compounds according to the invention, $R^x$ and $R^y$ are independently $C_{1-4}$ alkyl. In yet a further embodiment, $R^x$ and $R^y$ are methyl.

In one embodiment of the compounds according to the invention, L is selected from the group consisting of O, S, and CH$_2$. In another embodiment, L is selected from the group consisting of O and CH$_2$. In still another embodiment, L is O.

In a further embodiment of the compounds according to the invention, Z$^1$ is CH. In still a further embodiment, Z$^1$ is CH and L is O. In yet a further embodiment, Z$^1$ is CH, Z$^2$ is CH, and L is O.

In another embodiment of the compounds according to the invention, R$^3$ is selected from the group consisting of H, halo, and C(O)NH$_2$. In still another embodiment, R$^3$ is selected from the group consisting of halo and C(O)NH$_2$. In yet another embodiment, R$^3$ is selected from the group consisting of Cl and C(O)NH$_2$. In a further embodiment, R$^3$ is Cl.

In one embodiment of the compounds according to the invention having formula Ia, IIa, IIIa, or IVa, R$^2$ is H.

In another embodiment, the compounds of formula IVa have the following formula V:

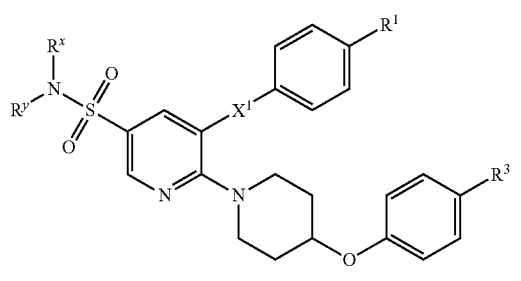

X$^1$, Y$^1$, R$^x$, R$^y$, R$^1$, and R$^3$ are as defined for the compounds of formula I and formula Ia. In a further embodiment of the compounds of formula V, X$^1$ is O, R$^1$ is C$_{1-4}$ alkyl-O—, R$^3$ is halo or C(O)NH$_2$, and R$^x$ and R$^y$ are independently C$_{1-4}$ alkyl.

In a presently preferred embodiment, the compound according to the present invention is selected from the group consisting of:

(1)
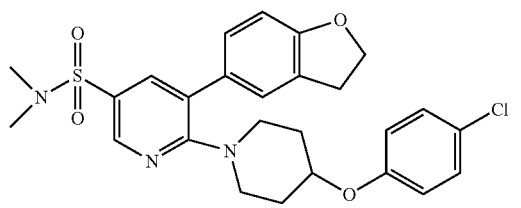

(2)
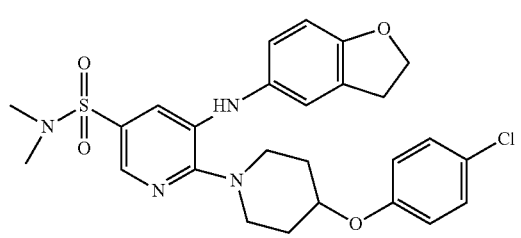

-continued (3)
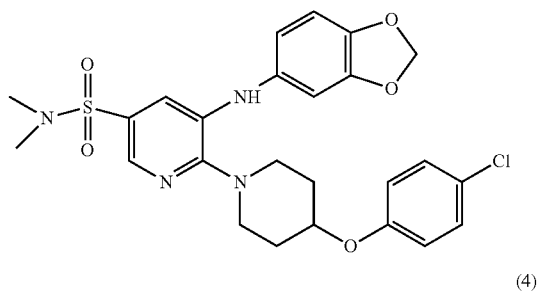

(4)
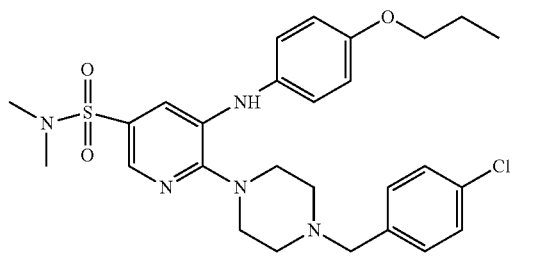

(5)
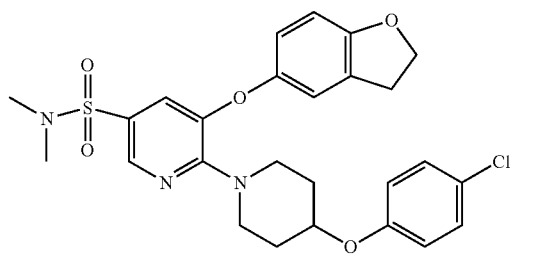

(6)
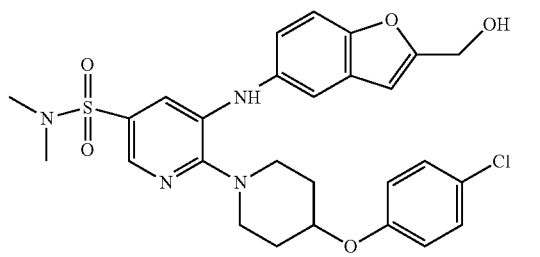

(7)
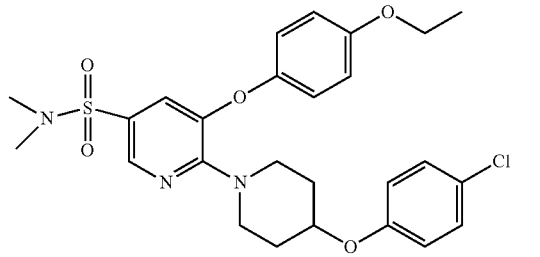

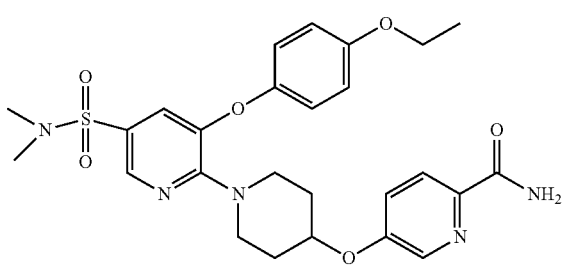
(8)

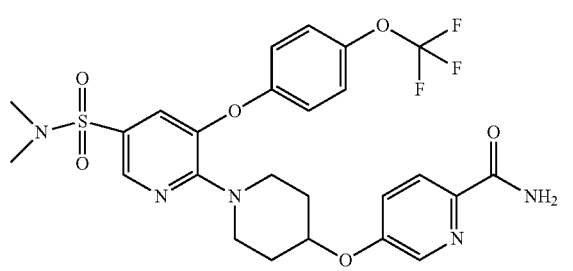
(9)

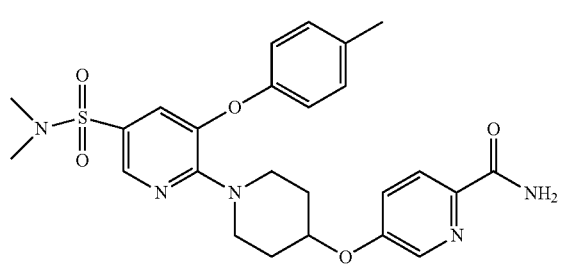
(10)

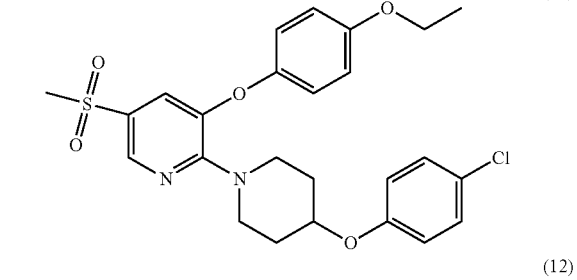
(11)

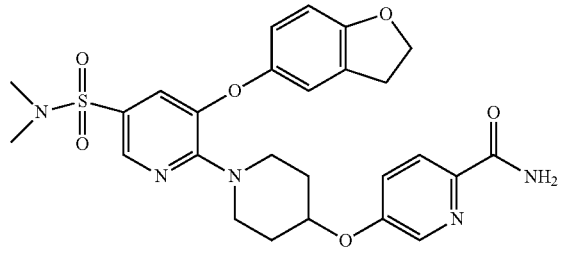
(12)

Pharmaceutical Formulation

The compounds of the present invention are intended for use as a medicament. The compounds of the invention may in principle be applied on their own, but they are preferably formulated with a pharmaceutically acceptable carrier. A pharmaceutically acceptable carrier is an inert carrier suitable for each administration method, and can be formulated into conventional pharmaceutical preparation (tablets, granules, capsules, powder, solution, suspension, emulsion, injection, infusion, etc.). As such a carrier there may be mentioned, for example, a binder, an excipient, a lubricant, a disintegrant and the like, which are pharmaceutically acceptable. When they are used as an injection solution or an infusion solution, they can be formulated by using distilled water for injection, physiological saline, an aqueous glucose solution.

The administration method of the compounds of the present invention is not particularly limited, and a usual oral or parenteral administration method (intravenous, intramuscular, subcutaneous, percutaneous, intranasal, transmucosal, enteral, etc.) can be applied.

The dosage of the tetrahydroisoquinoline derivatives or a pharmaceutically acceptable salt thereof of the present invention may optionally be set in a range of an effective amount sufficient for showing a pharmacological effect, in accordance with the potency or characteristics of the compound to be used as an effective ingredient. The dosage may vary depending on administration method, age, body weight or conditions of a patient.

Pharmaceutical Utility

The compounds of the invention are intended for the treatment of diseases responsive to inhibition of IL-1β such as non-alcoholic steatohepatitis (NASH) and idiopathic pulmonary fibrosis (IPF). Hence, in one aspect, the invention concerns a compound or composition according to the invention for use as a medicament. In a further aspect, the invention concerns a compound or composition according to the invention for use in the treatment of diseases responsive to inhibition of IL-1β such as non-alcoholic steatohepatitis (NASH) and idiopathic pulmonary fibrosis (IPF). In one embodiment, the disease responsive to inhibition of IL-1β is selected from the group consisting of non-alcoholic steatohepatitis (NASH), idiopathic pulmonary fibrosis (IPF), autoinflammatory diseases, cardiovascular diseases, osteoarthritis, lung cancer and gout. In a further embodiment, the disease is NASH. In still a further embodiment, the disease is IPF.

Preparation of Compounds—$X^1$ as $NR^y$

The substituted pyridine-sulfonamides of formula II and IIa of the present invention are generally prepared via intermediate C, which is prepared as outlined in Scheme 1:

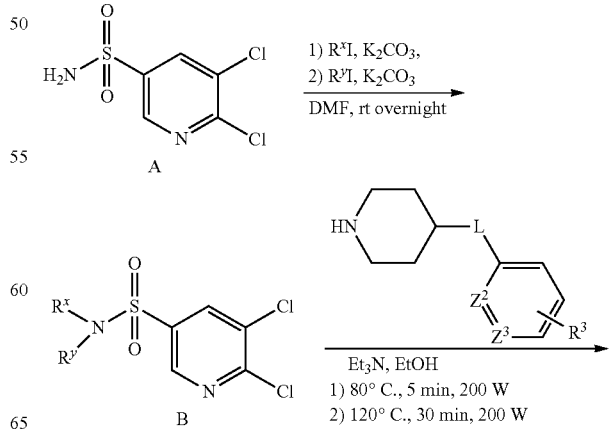

Scheme 1

13

-continued

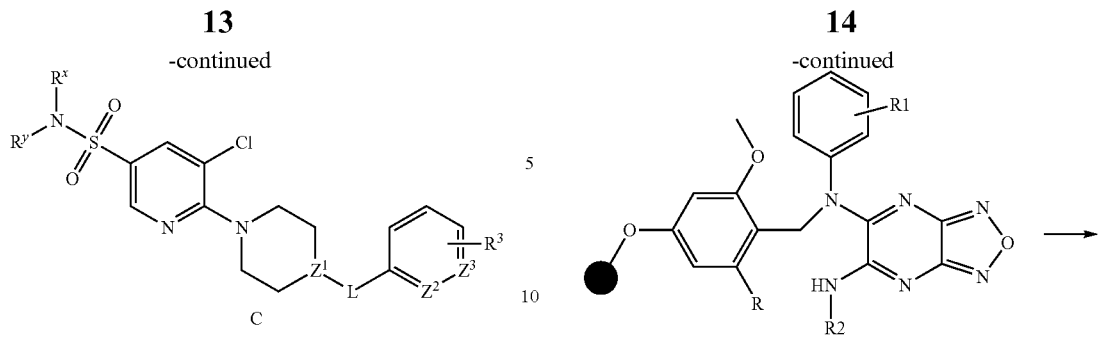

In a first step 5,6-dichloropyridin-3-sulfonamide A is alkylated to get intermediate compound B, which is then transformed in compound C through a Buchwald-type reaction with the corresponding bicyclic amine under microwave irradiation.

14

-continued

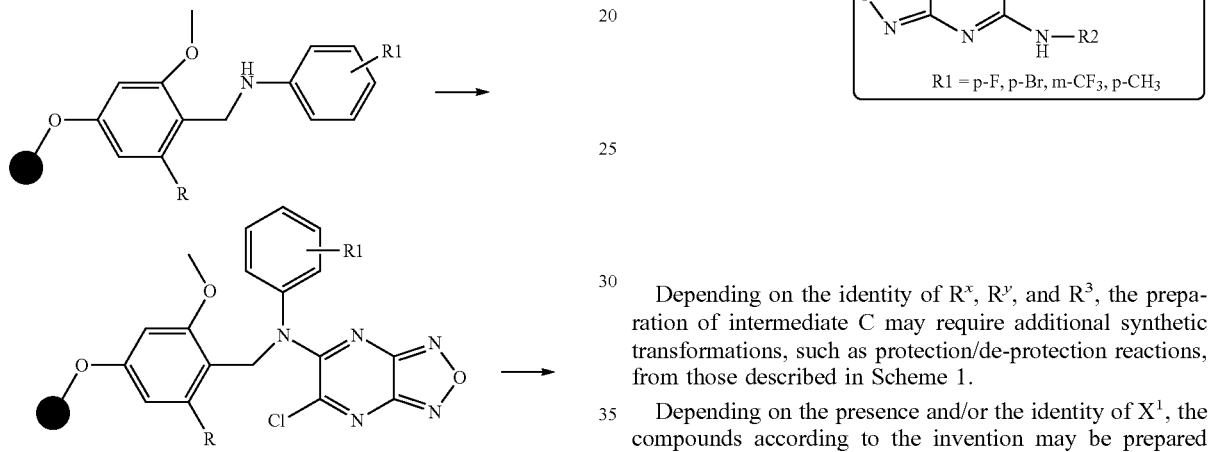

R1 = p-F, p-Br, m-CF3, p-CH3

Depending on the identity of $R^x$, $R^y$, and $R^3$, the preparation of intermediate C may require additional synthetic transformations, such as protection/de-protection reactions, from those described in Scheme 1.

Depending on the presence and/or the identity of $X^1$, the compounds according to the invention may be prepared according to Schemes 2b, 2c, or 2d.

Scheme 2b - Synthesis of compound type IIb

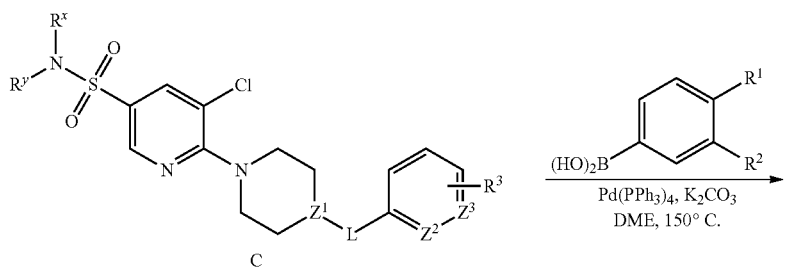

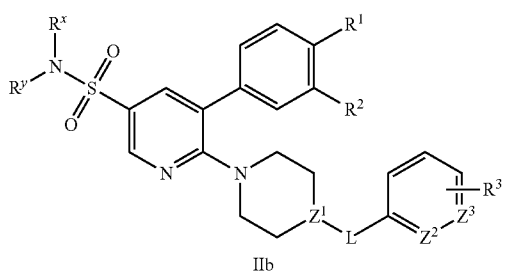

IIb

A Pd-catalyzed Suzuki-type reaction of intermediate compound C with the corresponding boronic acid at 150° C. under microwave irradiation leads to compounds of type IIb (such as compound 1; synthetic procedure as in *Bioorg. Med. Chem. Lett.* 2011, 21(10), 3152-3158).

Scheme 2c - Synthesis of compound type IIc

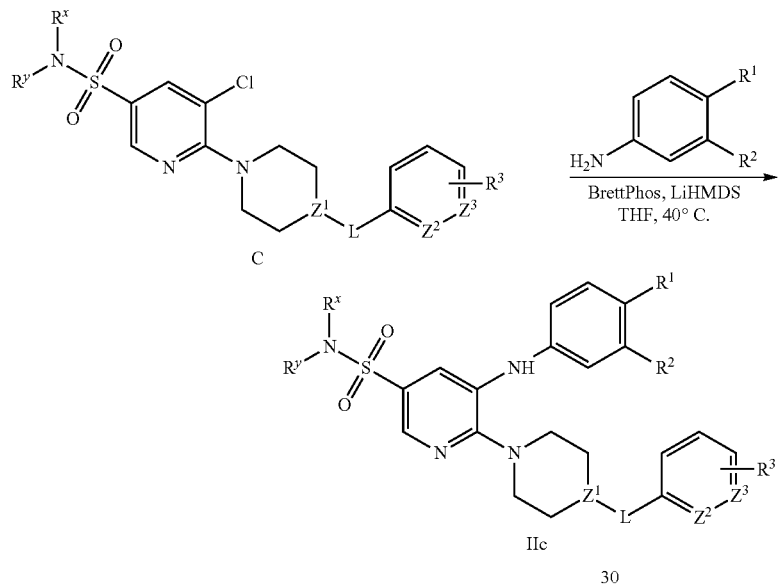

Pd-catalyzed Buchwald reaction of intermediate compound C with substituted anilines at 40° C. in the presence of a strong base yields compounds of type IIc (such as compounds 2, 3, 4, 6; synthetic procedure as in see *Org. Lett.* 2011, 13(8), 1984-1987).

Scheme 2d - Synthesis of compound type IId

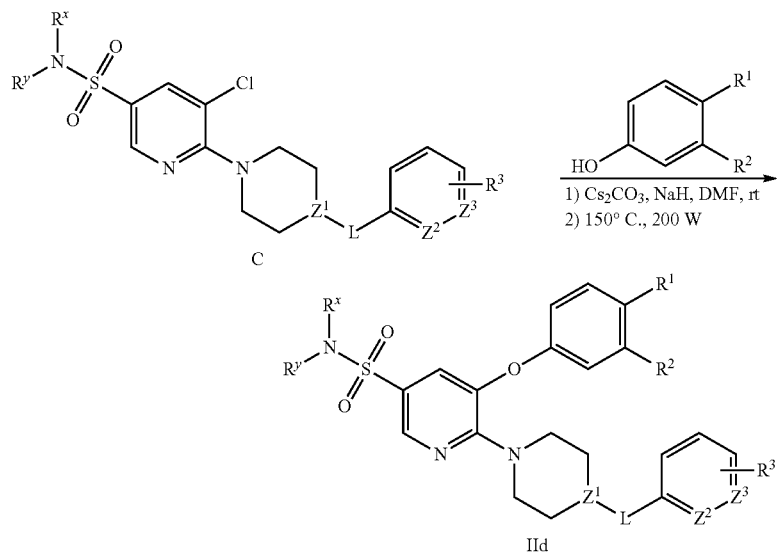

Compounds of type IId (such as compounds 5, 7, 8, 9, 10, 12) are obtained through an Ullman-type reaction of intermediate C with the corresponding phenol in the presence of sodium hydride and cesium carbonate at 150° C. under microwave irradiation (synthetic procedure as in *J. Am. Chem. Soc.* 2013, 135(24), 9213-9219).

Preparation of Compounds—X³ is Absent

The substituted pyridine-sulfonamides of formula I and Ia of the present invention, wherein X³ is absent, are generally prepared via intermediate E, which is prepared as outlined in Scheme 3:

Scheme 3 - Synthetic procedure for compound E

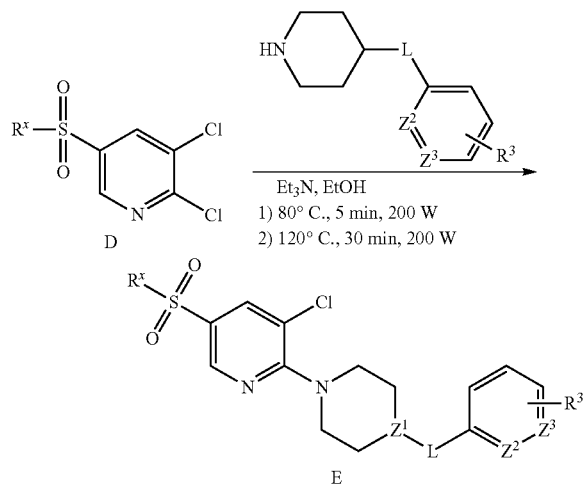

Analogous procedure to the preparation of intermediate compound C but using D-type compound as the starting material, for example 2,3-dichloro-5-(methylsulfonyl)pyridine in the case of the synthesis of final compound 11.

EXAMPLES

Example 1—Synthesis of intermediate B having $R^x$ and $R^y$ as methyl: N,N-dimethyl-5,6-dichloropyridin-3-sulfonamide To a suspension of commercially available 5,6-dichloropyridin-3-sulfonamide A (1 eq) and $K_2CO_3$ (2 eq) in anhydrous DMF (1 ml/eq) iodomethane (2 eq) in DMF (5 ml/mmol) was added and the resulting mixture was stirred at room temperature until reaction was completed (overnight, TLC control). Then the solvent was evaporated and ethyl acetate was added. The organic mixture was washed twice with water and the organic layer was dried with magnesium sulphate. After evaporation of the solvent the resulting crude product was pure enough to be used in Example 2 without purification (yellow solid, 95% yield)

Example 2—Synthesis of intermediate C having $R^x$ and $R^y$ as methyl, $Z^1$, $Z^2$, $Z^3$ as CH, L as O, and $R^3$ as Cl in the para position: N,N-dimethyl-5-chloro-6-(4-(4-chlorophenoxy)-N-piperidinyl)-pyridin-3-sulfonamide A mixture of the compound obtained in Example 1 (1 eq), commercially available 4-(4-chlorophenoxy)piperidine hydrochloride (1.2 eq) and TEA (2.2 eq) in EtOH (4.8 ml/mmol) was heated first at 80° C. for 5 min and then at 120° C. for 30 min under microwave irradiation (200 W) (HPLC control). Then the solvent was evaporated and ethyl acetate was added; the organic mixture was washed twice with water and the combined organic layers were dried with magnesium sulphate. After that solvent was evaporated and the resulting crude product was pure enough to be used in subsequent Examples without purification (clear brown solid, 91% yield).

Example 3—Synthesis of intermediate C having $R^x$ and $R^y$ as methyl, $Z^1$, $Z^3$ as CH, $Z^2$ as N, L as O, and $R^3$ as C(O)NH₂ in the para position: N,N-dimethyl-5-chloro-6-[4-(5-[2-carboxamido-pyridin]yloxy)-N'-piperidinyl]-pyridin-3-sulfonamide A mixture of the compound obtained in Example 1 (1 eq), commercially available 4-(piperidin-4-yloxy)pyridine-2-carboxamide (1.2 eq) and TEA (2.2 eq) in EtOH (4.8 ml/mmol) was heated first at 80° C. for 5 min and then at 120° C. for 30 min under microwave irradiation (200 W) (HPLC control). Then the solvent was evaporated and ethyl acetate was added; the organic mixture was washed twice with water and the combined organic layers were dried with magnesium sulphate. After that solvent was evaporated and the resulting crude product was enough pure to be used in the next step without purification (clear white solid, 93% yield).

Example 4—Synthesis of Compound 1

A solution of the intermediate obtained in Example 2 (1 eq.), benzo[b]furan-5-boronic acid (1.1 eq), potassium carbonate (1.4 eq) and $Pd(PhPh_3)_4$ (0.1 eq) in DME (5 ml/mmol) was heated at 150° C. under microwave irradiation (200 W) for 1 h (or overnight at 150° C.). Then the crude mixture was diluted with EtOAc, filtered through a Celite plug, washed with EtOAc and MeOH, and the solvent was evaporated. The resulting crude product was purified by Isolera Biotage system (C18, acetonitrile/water) to yield pure product. White foam, 45% total yield, 98% HPLC purity.

1HNMR ($CDCl_3$, 400 MHz): δ (ppm)=8.51 (d, 1H), 7.68 (d, 1H), 7.33 (s, 1H), 7.27 (s, 1H), 7.22 (d, 2H), 6.86-6.81 (m, 3H), 4.64 (t, 2H), 4.42-4.38 (m, 2H), 3.61-3.55 (m, 2H), 3.27 (t, 2H), 3.19-3.18 (m, 2H), 2.76 (s, 6H), 1.94-1.89 (m, 2H), 1.76-1.70 (m, 2H). $C_{26}H_{29}ClN_3O_4S$ MS (electrospray): m/z=514.1583 (M+1).

Example 5—Synthesis of Compound 2

A screw-cap test-tube, equipped with a magnetic stir bar, was charged with BrettPhos-precatalyst (4 mol %), 2,3-dihydrobenzo[b]furan-5-amine (1 eq.) and the intermediate compound obtained in Example 2 (1 eq.). The vial was sealed with a teflon screw-cap, evacuated and backfilled with nitrogen; this procedure was repeated two additional times. Then, LiHMDS (1M in THF, 2.5 eq.) was added. The reaction mixture was stirred at 40° C. until reaction was completed (2.5 h). The solution was allowed to cool to room temperature, quenched by the addition of aqueous, saturated $NH_4Cl$ solution (5 mL) and then diluted with EtOAc. The organic phase was separated and the aqueous phase was extracted one more time with EtOAc. The combined organic phases were washed with brine and dried over MgSO4. The solvent was removed under reduced pressure and the crude was purified by Isolera Biotage System (C18, acetonitrile/water) yielding impure product (115.7 mg), which was purified again by the same system. Brown solid, 6% total yield, 96% HPLC purity (254 nm).

1HNMR ($CDCl_3$, 400 MHz): δ (ppm)=8.34 (s, 1H), 7.96 (bs, 1H), 7.24 (dd, 2H), 7.03 (s, 1H), 6.96 (dd, 1H), 6.85-6.79 (m, 3H), 5.88 (s, 1H), 4.63 (t, 2H), 4.48 (m, 1H), 3.76-3.73 (m, 2H), 3.45 (m, 2H), 3.23 (t, 2H), 2.80 (s, 6H), 1.99-1.94 (m, 2H), 1.82 (m, 2H). $C_{26}H_{30}ClN_4O_4S$, MS (electrospray): m/z=529.1677 (M+1).

Example 6—Synthesis of Compound 5

2,3-dihydro-5-hydroxybenzo[b]furan (1.1 eq) and cesium carbonate (1.2 eq) were taken in anhydrous DMF (1.2 ml/mmol) and treated with neat sodium hydride (1.1 eq). After hydrogen evolution ceased, the intermediate compound obtained in Example 2 (1 eq) was added and the reaction was stirred at 150° C. until no further evolution of reaction in a sealed pressure tube (overnight) or under microwave irradiation (200 W) (2 h). Then solvent was removed under vacuum and the crude product was diluted with ethyl acetate (6 ml/mmol) and water (6 ml/mmol). The aqueous layer was extracted with ethyl acetate three times. The organic layer was washed with 2N NaOH, dried and concentrated under vacuum. Crude product was purified by Isolera Biotage system (C18, acetonitrile-water gradient) to yield impure product, which was purified by preparative chromatography (silica, hexane/ethyl acetate 4:1). Clear oil, 12% total yield, 100% HPLC purity (254 nm).

1HNMR (CDCl$_3$, 400 MHz): δ (ppm)=8.30 (dd, 1H), 7.247-7.22 (m, 3H), 6.86-6.81 (m, 3H), 6.75-6.70 (m, 2H), 4.61 (t, 2H), 4.50-4.47 (m, 1H), 4.00-3.97 (m, 2H), 3.66-3.63 (m, 2H), 3.21 (t, 2H), 2.67 (s, 6H), 2-06-1.99 (m, 2H), 1.90-1.84 (m, 2H). $C_{26}H_{28}ClN_3O_5S$ MS (electrospray): m/z=530.1550 (M+1).

Example 7—Synthesis of Compound 7

4-ethoxyphenol (1.1 eq) and cesium carbonate (1.2 eq) were taken in anhydrous DMF (1.2 ml/mmol) and treated with neat sodium hydride (1.1 eq). After hydrogen evolution ceased, the intermediate obtained in Example 2 (1 eq) was added and the reaction was stirred at 150° C. until no further evolution of reaction in a sealed pressure tube (overnight) or under microwave irradiation (200 W) (2 h). Then solvent was removed under vacuum and the crude product was diluted with ethyl acetate (6 ml/mmol) and water (6 ml/mmol). The aqueous layer was extracted with ethyl acetate three times. The organic layer was washed with 2N NaOH, dried and concentrated under vacuum. Crude product was purified by Isolera Biotage system (C18, acetonitrile-water gradient), recovering unreacted starting material and pure product. Clear brown solid, 41% yield, 100% HPLC purity (254 nm).

1HNMR (CDCl$_3$, 400 MHz): δ (ppm)=8.31 (d, 1H), 7.26-7.23 (m, 4H), 6.88-6.84 (m, 5H), 4.51-4.46 (1H, m), 4.05-4.00 (m, 4H), 3.66-3.59 (m, 2H), 2.67 (s, 6H), 2.00-1.86 (m, 2H), 1.86-1.83 (m, 2H), 0.43 (t, 3H). $C_{26}H_{30}ClO_5S$ MS (electrospray): m/z=532.1680 (M+1).

Example 8—Synthesis of Compound 8

4-ethoxyphenol (1.1 eq) and cesium carbonate (1.2 eq) were taken in anhydrous DMF (1.2 ml/mmol) and treated with neat sodium hydride (1.1 eq). After hydrogen evolution ceased, the intermediate obtained in Example 3 (1 eq.) was added and the reaction was stirred at 150° C. until no further evolution of reaction in a sealed pressure tube (overnight) or under microwave irradiation (200 W) (3 h). Then solvent was removed under vacuum and the crude product was diluted with ethyl acetate (6 ml/mmol) and water (6 ml/mmol). The aqueous layer was extracted with ethyl acetate three times. The organic layer was washed with 2N NaOH, dried and concentrated under vacuum. Crude product was purified by Isolera Biotage system (C18, acetonitrile-water gradient), recovering unreacted starting material and pure product. Clear brown solid, 16% yield, 100% HPLC purity (254 nm).

1HNMR (CDCl$_3$, 400 MHz): δ (ppm)=8.38 (d, 1H), 8.34 (s, 1H), 6.98-6.97 (m, 1H), 6.89 (s, 1H), 5.59 (bs, 1H), 4.79-4.75 (m, 1H), 4.06-3.63 (m, 4H), 3.69-3.63 (m, 2H), 2.68 (s, 6H), 2-10-2.06 (m, 2H), 1.92-1.88 (m, 2H), 1.44 (t, 3H). $C_{26}H_{31}N_5O_6S$ MS (electrospray): m/z=542.2084 (M+1).

Example 9—Synthesis of Compound 12

2,3-dihydro-5-hydroxybenzo[b]furan (1.1 eq) and cesium carbonate (1.2 eq) were taken in anhydrous DMF (1.2 ml/mmol) and treated with neat sodium hydride (1.1 eq). After hydrogen evolution ceased, the intermediate obtained in Example 3 (1 eq) was added and the reaction was stirred at 150° C. until no further evolution of reaction in a sealed pressure tube (overnight) or under microwave irradiation (200 W) (2.5 h). Then solvent was removed under vacuum and the crude product was diluted with ethyl acetate (6 ml/mmol) and water (6 ml/mmol). The aqueous layer was extracted with ethyl acetate three times. The organic layer was washed with 2N NaOH, dried and concentrated under vacuum. Crude product was purified by IoleraBiotage system (C18, acetonitrile-water gradient), recovering unreacted starting material and pure product. White foam, 13% yield, 98% HPLC purity (254 nm).

1HNMR (CDCl$_3$, 400 MHz): δ (ppm)=8.38 (d, 1H), 8.31 (d, 1H), 7.24 (d, 1H), 6.97-6.96 (m, 1H), 6.82 (d, 1H), 6.76-6.69 (m, 2H), 5.63 (bs, 1H), 4.79-4.76 (m, 2H), 4.62 (t, 2H), 4.02-4.00 (m, 2H), 3.68-3.63 (m, 2H), 3.22 (t, 2H), 2.68 (s, 6H), 2.12-2.08 (m, 2H), 1.93-1.89 (m, 2H). $C_{26}H_{29}N_5O_6S$ MS (electrospray): m/z=540.1944 (M+1).

Example 10—Synthesis of intermediate E having $R^x$ methyl, $Z^1$, $Z^2$, $Z^3$ as CH, L as O, and $R^3$ as Cl in the para position: 3-chloro-2-[4-(4-chlorophenoxy)-N-piperidinyl]-5-methylsulfonyl-pyridine Analogous procedure to the synthesis of the intermediate compound according to Example 2, but using commercially available 2,3-dichloro-5-(methylsulfonyl)pyridine as starting material. White solid, 96% total yield.

Example 11—Synthesis of Compound 11

Analogous procedure to the synthesis of compounds 5, 7, 8, and 12 in Examples 6 to 9, but using the intermediate compound obtained in Example 10 as starting material. 6 h. Clear oil, 16% total yield, 95% HPLC purity (254 nm).

1HNMR (CDCl$_3$, 400 MHz): δ (ppm)=8.45 (s, 1H), 7.35 (d, 1H), 7.26 (dd, 2H), 6.85 (d, 2H), 4.52-4.48 (m, 1H), 4.04-4.00 (m, 4H), 3.72-3.66 (m, 2H), 3.01 (s, 3H), 2.05-1.99 (m, 2H), 1.90-1.84 (m, 2H), 1.43 (t, 3H). $C_{25}H_{28}ClN_2O_5S$ MS (electrospray): m/z=503.1398 (M+1).

Example 12—In Vitro Inhibition of IL-1β in Human Primary Macrophages Challenged with LPS Materials

| S.No | Materials | Catalog Number | Supplier |
|---|---|---|---|
| 1 | LEGEND MAX human IL-1β ELISA kit | 437008 | Biolegend |
| 2 | RPMI 1640 cell culture medium | R6504 | Sigma-Aldrich |
| 3 | Phosphate buffered saline | P3813 | Sigma-Aldrich |
| 4 | Dimethyl Sulfoxide | D2650 | Sigma-Aldrich |
| 5 | Foetal Bovine Serum | 10270-106 | Gibco |
| 6 | Penicillin-Streptomycin | 15140-122 | Gibco |
| 7 | Histopaque-1077 | 10771 | Sigma-Aldrich |
| 8 | Sodium Citrate Tribasic Solution | 91150 | Sigma-Aldrich |
| 9 | 'V' bottom polypropylene 96 well Micro Plate | 15160 | Griener |
| 10 | Recombinant human GM-CSF | 572902 | Biolegend |
| 11 | LipoPolySaccharide (LPS) | L6529 | Sigma-Aldrich |
| 12 | CellTiter-Glo ® luminescent assay kit | G7570 | Promega |

Preparation of RPMI 1640 Growth Medium

RPMI 1640 basal medium was prepared according to the manufacturer's instructions on the data sheet. A sterility check was carried out using 5 mL of medium for 48 hours at 37° C. incubator with constant supply of 5% $CO_2$. Following the sterility check, the basal medium was made complete by addition of FBS and Pen/Strep antibiotic. The medium was stored at 4° C. until further use.

Preparation of Phosphate-Buffered Saline (PBS)

A single sachet of PBS was dissolved in a litre of Milli-Q water. PBS was filtered through a 0.22 μm filter membrane and stored at 4° C. until further use.

Preparation of Peripheral Blood Mononuclear Cells (PBMC)

5 mL of RPMI media without serum (1:1) was added to a sample of 5 mL of human whole blood in EDTA or sodium citrate and mixed well by inversion. 3 mL of Histopaque-1077 was added to a 15 mL conical centrifuge tube and brought to room temperature. Using a transfer pipette, 10 mL of the blood-RPMI mixture was carefully layered onto the Histopaque-1077 and was centrifuged at 400×g for exactly 30 minutes at room temperature.

After centrifugation, a pasteur pipette was used to aspirate the upper layer to within 0.5 cm of the opaque interface containing the mononuclear cells. The upper layer was discarded. With a Pasteur pipette, the opaque interface was carefully transferred to a clean conical centrifuge tube. 5 mL RPMI was added to the tube and mixed by inversion, followed by centrifugation at 250×g for exactly 10 minutes. The supernatant was aspirated and discarded.

The leukocyte pellet was re-suspended with 5 mL RPMI and mixed gently with a Pasteur pipette, followed by centrifugation at 250×g for exactly 10 minutes. The pellet was washed 3× with PBS and re-suspended in RPMI medium.

The number of viable PBMCs/mL was counted.

Counting PBMCs

10 μL of PBMC suspension was diluted with 90 μL of PBS medium (1:10 dilution). 20 μL of cell suspension was added to 20 μL of trypan blue solution (1:1 ratio) and was mixed carefully to avoid aerosol formation. A haemocytometer was loaded with cell culture mixture until the area under the coverslip was sufficiently filled. The suspension was allowed to settle in the haemocytometer for at least 10 seconds before counting.

The viable cells were counted in four corner 1 mm squares of one chamber, as well as the number of dead cells. Viable PBMCs are clear; non-viable PBMCs are blue. Cells that touched either the top line or vertical perimeter line of any corner square were included. Cells that touched either the bottom line or right vertical perimeter line of any corner square were not counted.

Calculation of Cell Count

Calculation of the number of viable PBMCs/mL:

$$PBMC/mL = PBMC \text{ in all four squares} \times 10 \times 2 \times 10^4 / 4$$

$10^4$ = Volume conversion factor to 1 mL;
10 = dilution factor of cell suspension;
2 = Dilution factor with trypan blue $$\text{Total cell count} = PBMC/mL \times \text{Total volume (mL) of PBMC suspension}$$

$$\% \text{ Cell viability} = (\text{Number of viable cells counted}/\text{total number of cells counted (viable+dead)}) \times 100$$

Cell Seeding, Differentiation and Treatment $2 \times 10^5$ PBMCs at a total volume of 200 μL/well were plated into a 96-well plate and incubated for 4 hrs at 37° C. in a $CO_2$ incubator to allow the monocytes to settle, leaving the lymphocytes in suspension. Following incubation, 100 μL were aspirated out of each well to ensure removal of the lymphocyte population.

The monocytes were differentiated to macrophages by addition of 200 ng/mL of recombinant human GM-CSF (4 mg/mL stock) and incubated at 37° C./5% $CO_2$ for 6 days. The medium was changed every two days by removing half the volume of medium in the well and re-supplementing with fresh RPMI complete medium and recombinant human GM-CSF.

Following differentiation, the cells were treated in duplicates with a compound according to the invention in a total volume of 50 μL, maintaining a final DMSO percentile of 0.5%. The plate was transferred to an incubator maintained at 37° C./5% $CO_2$ for 2 hours. The cells were stimulated with 100 ng/mL of LPS (4×) (1 mg/mL stock) in a total volume of 50 μL.

The plate was transferred to an incubator maintained at 37° C./5% $CO_2$ for 16 hours.

Cytokine Estimation by ELISA

1. Each well from a pre-coated ELISA plate was aspirated and washed with wash buffer (0.05% Tween 20 in PBS; pH 7.2-7.4) by filling each well with wash buffer (300 μL). The process was repeated two times for a total of three washes. The liquid was removed completely at each step. After the last wash, any remaining wash buffer was removed.
2. Plates were blocked by adding 300 μL of block buffer (1% BSA in PBS) to each well and incubated at room temperature for 1 hour.
3. The aspiration/wash as in step 1 was repeated.
4. 100 μL of sample or standard prepared in reagent diluent (0.1% BSA, 0.05% Tween 20 in PBS pH7.2-7.4) was added. The wells were covered with an adhesive strip and incubated for 2 hours at room temperature.
5. The aspiration/wash as in step 1 was repeated.

6. 100 µL of detection antibody, diluted in reagent diluent, was added to each well. The wells were covered with a new adhesive strip and incubated for 2 hours at room temperature.
7. The aspiration/wash as in step 1 was repeated.
8. 100 µL of the working dilution (1:200 from the stock) and streptavidin-HRP was added to each well. The plate was covered and incubated for 20 minutes at room temperature.
9. 100 µL of substrate solution (1:1 mixture of $H_2O_2$ and tetramethylbenzidine) was added to each well and incubated for 20 minutes at room temperature.
10. 50 µL of stop solution (2N $H_2SO_4$) was added to each well. The plate was tapped gently to ensure thorough mixing.
11. The optical density of each well was determined immediately using a microplate reader (Spectramax Plus) set to 450 nm.

Cytokine Viability Assessment

100 µl/well volume of CellTiter-Glo® luminescent reagent was added to the assay plates and incubated at room temperature for 30 mins on a plate shaker. Following incubation, the luminescent signal of each well was determined using a microplate reader (Perkin Elmer ENVISION 2104).

Data Analysis

% Inhibition of the test compounds was determined utilizing the following formula:

% Inhibition=100−(100*(Average Test Compound Counts−Average Negative Control Counts)/(Average Positive Control Counts−Average Negative Control Counts))

All of the "Counts" stated in this formula are derived from "Optical Density values" determined as described above using the microplate reader (step 11).

Cytotoxicity of the test compounds was determined utilizing the following formula:

% Cytotoxicity=100−(100*(Average Test Compound Counts−Average Negative Control Counts)/(Average Positive Control Counts−Average Negative Control Counts))

All of the "Counts" stated in this formula are derived from "luminescent signal" determined as described for the cytokine viability assessment.

Results

|  | IC50 (IL-Iβ inhibition) | Cell viability |
| --- | --- | --- |
| Compound 1 | 115 nM | 100% |
| Compound 2 | 29 nM | 100% |
| Compound 3 | 121 nM | 100% |
| Compound 4 | 300 nM | 100% |
| Compound 5 | 28 nM | 100% |
| Compound 6 | 13 nM | 100% |
| Compound 7 | 27 nM | 100% |
| Compound 8 | 337 nM | 100% |
| Compound 9 | 531 nM | 100% |
| Compound 10 | 410 nM | 100% |
| Compound 11 | 753 nM | 100% |
| Compound 12 | 2.3 µM | 100% |

Example 13—In Vitro Binding of JNK1 (MAPK8)

Various concentrations of Recombinant Human MAPK8 dissolved in water were manually printed onto a bare gold-coated (thickness 47 nm) PlexArray Nanocapture Sensor Chip (Plexera Bioscience, Seattle, WA, US) at 40% humidity. Each concentration was printed in replicate, and each spot contained 0.2 µL of the protein solution. The chip was incubated in 80% humidity at 4° C. overnight, and rinsed with 10×PBST for 10 min, 1×PBST for 10 min, and deionized water twice for 10 min. The chip was then blocked with 5% (w/v) non-fat milk in water overnight, and washed with 10×PBST for 10 min, 1×PBST for 10 min, and deionized water twice for 10 min before being dried under a stream of nitrogen prior to use.

Surface Plasmon Resonance Imaging (SPRi) measurements were performed with PlexArray HT (Plexera Bioscience, Seattle, WA, US). Collimated light (660 nm) passes through the coupling prism, reflects off the SPR-active gold surface, and is received by the CCD camera. Buffers and samples were injected by a non-pulsatile piston pump into the 30 µL flowcell that was mounted on the coupling prism. Each measurement cycle contained four steps: washing with PBST running buffer at a constant rate of 2 µL/s to obtain a stable baseline, sample injection at 5 µL/s for binding, surface washing with PBST at 2 µL/s for 300 s, and regeneration with 0.5% (v/v) $H_3PO_4$ at 2 µL/s for 300 s. All the measurements were performed at 4° C.

The signal changes after binding and washing were recorded in AU as the assay value. Selected protein-grafted regions in the SPR images were analyzed, and the average reflectivity variations of the chosen areas were plotted as a function of time. Real-time binding signals were recorded and analyzed by Data Analysis Module (DAM, Plexera Bioscience, Seattle, WA, US). Kinetic analysis was performed using BIAevaluation 4.1 software (Biacore, Inc.).

The equilibrium dissociation constant (KD Value) determined for Compound 7 was $3.41 \times 10^{-8}$ M. (Ka=$2.29 \times 10^4$ $M^{-1} \cdot s^{-1}$, Kd=$7.82 \times 10^{-4} s^{-1}$)

Example 14—In Vitro Binding of p38 MAPK

Various concentrations of p38 MAPK dissolved in water were manually printed onto a bare gold-coated (thickness 47 nm) PlexArray Nanocapture Sensor Chip (Plexera Bioscience, Seattle, WA, US) at 40% humidity. Each concentration was printed in replicate, and each spot contained 0.2 µL of protein solution. The chip was incubated in 80% humidity at 4° C. for overnight, and rinsed with 10×PBST for 10 min, 1×PBST for 10 min, and deionized water twice for 10 min. The chip was then blocked with 5% (w/v) non-fat milk in water overnight, and washed with 10×PBST for 10 min, 1×PBST for 10 min, and deionized water twice for 10 min before being dried under a stream of nitrogen prior to use.

Surface Plasmon Resonance Imaging (SPRi) measurements were performed with PlexArray HT (Plexera Bioscience, Seattle, WA, US). Collimated light (660 nm) passes through the coupling prism, reflects off the SPR-active gold surface, and is received by the CCD camera. Buffers and samples were injected by a non-pulsatile piston pump into the 30 µL flowcell that was mounted on the coupling prism. Each measurement cycle contained four steps: washing with PBST running buffer at a constant rate of 2 µL/s to obtain a stable baseline, sample injection at 5 µL/s for binding, surface washing with PBST at 2 µL/s for 300 s, and regeneration with 0.5% (v/v) $H_3PO_4$ at 2 µL/s for 300 s. All the measurements were performed at 4° C.

The signal changes after binding and washing (in AU) are recorded as the assay value. Selected protein-grafted regions in the SPR images were analyzed, and the average reflectivity variations of the chosen areas were plotted as a function of time. Real-time binding signals were recorded and analyzed by Data Analysis Module (DAM, Plexera Bioscience, Seattle, WA, US). Kinetic analysis was performed using BIAevaluation 4.1 software (Biacore, Inc.).

The equilibrium dissociation constant (KD Value) determined for Compound 7 was $1.19 \times 10^{-8}$ M. ($Ka=2.08 \times 10^4$ $M^{-1} \cdot s^{-1}$, $Kd=2.48 \times 10^{-4} s^{-1}$)

Example 15: Effect of Compound 5 and 7 in the Treatment of Non-Alcoholic Steatohepatitis (NASH) in Male C57BL/6 Mice NASH Induction Timed pregnant mice (n=30) were selected for the study. The delivered pups were subcutaneously injected on the post-natal day 2 (PND-2) with 200 μg of Streptozotocin and were allowed to remain with the mother until they reached the weanling age. After weanling, the male pups were selected and fed with 60% kcal fat diet (Research Diet-D12492) for the next 2 weeks. All the animals were observed twice daily for clinical signs.

Study Procedure

Mice were dosed with vehicle, test compounds and reference compound (elafibranor) twice daily morning (9.00 AM) and evening before the start of dark cycle (6:00 PM) from day 0 to 28.

Animal body weight measurements were made daily for the complete duration of the experiment.

Animals were dosed for 28 days (from week 6 to 10) with the test and reference compounds.

Blood glucose was estimated before the treatment start and on the termination day 28. Serum ALT and AST levels were measured from the plasma before the treatment start and on day 28.

Histopathology analysis including H&E staining, Masson's trichrome staining and Oil-Red-O (ORO) staining was performed for the liver tissues.

Sample Analysis

NAFLD (Non Alcoholic Fatty Liver Disease) Scoring: H&E Staining

All the H&E stained tissue sections were examined by light microscopy. As per the below grading system (Kleiner et al., 2005) in 200× objective lens, NAFLD scoring was done for steatosis, lobular inflammation and hepatic ballooning.

Collagen Proportion Area (% CPA) Measurement: Masson's Trichrome Staining

All the Masson's trichrome stained tissue sections were examined by light microscopy in 100× objective lens. Randomly selected five fields (approx 684.85 μm×917.11 m per field) from each liver were subjected to collagen proportion area measurement by using Image Pro Premier 9.1 software. The percentage of collagen proportion area was calculated by dividing collagen tissue area by total tissue area.

Percent Stained Area Measurement: Oil Red O staining

All the Oil-Red-O stained tissue sections were examined by light microscopy in 100× objective lens. Randomly selected five fields (approximately 688.33 μm×922.45 μm per field) from each liver were subjected to measure stained area by using Image Pro Premier 9.1 software. The percentage of stained area was calculated by dividing lipid stained tissue area by total tissue area.

The effect of Compound 5 and Compound 7 on NAFLD activity score (NAS) is shown in FIG. 1.

The study clearly demonstrated that Compound 7 at the 3 mg/kg dose significantly reduced steatosis and lobular inflammation in the liver and showed better NAS score than Elafibranor.

Compound 5 at the 3 mg/kg dose significantly reduced lobular inflammation and showed a trend towards decreased steatosis and hepatic ballooning resulting in significant reduced NAS score than disease controls.

Figure 2:
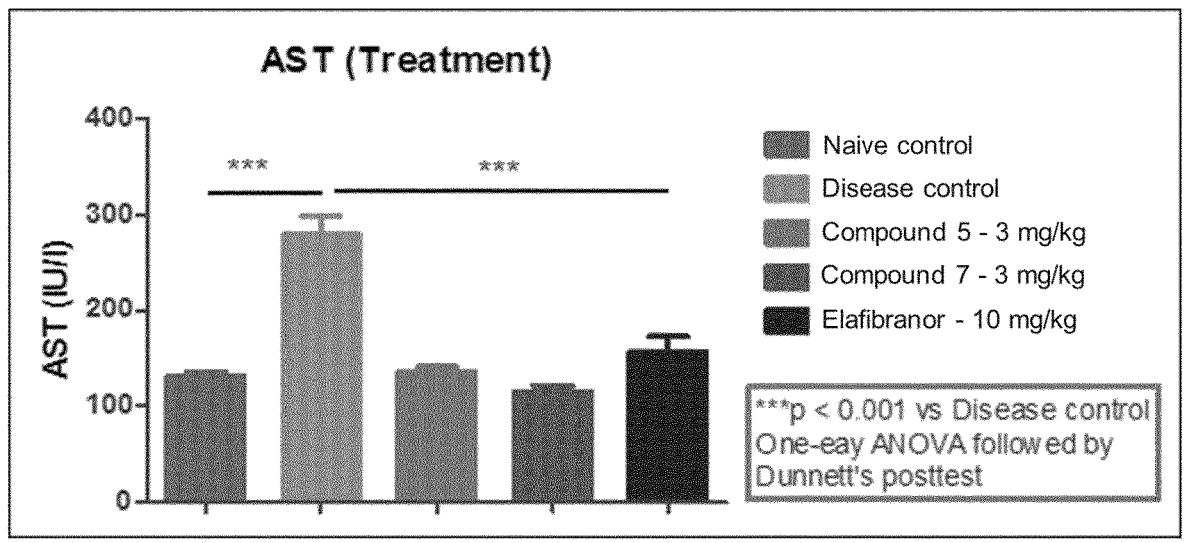
FIG. 2. Serum AST (U/L) levels after 28 days of treatment.

Compounds 5 and 7 exhibited significantly reduced levels of AST after 28 days of treatment as shown in FIG. 2

Figure 3:
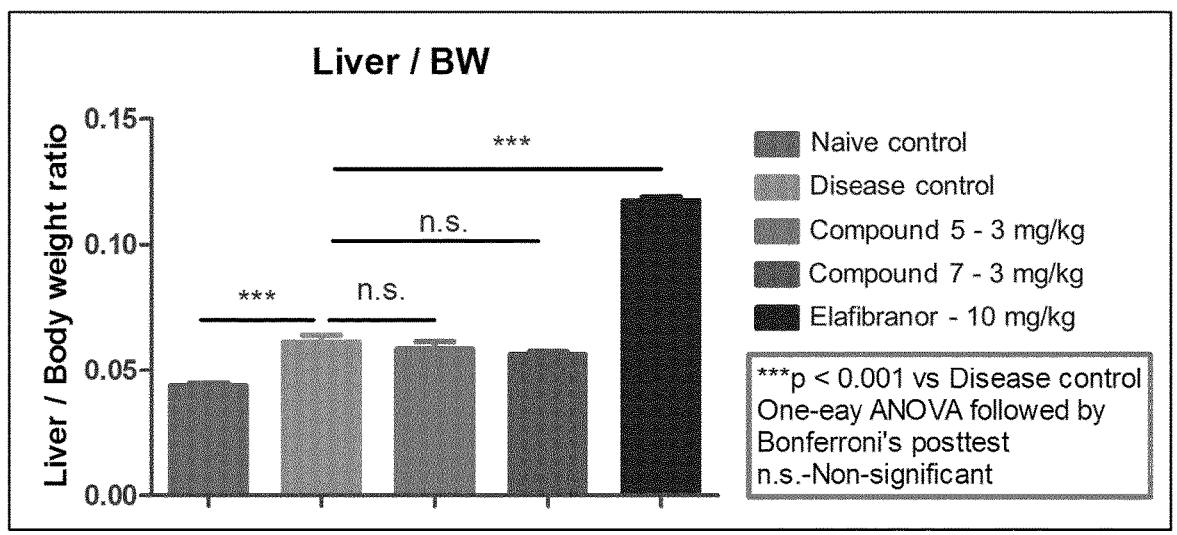
FIG. 3. Effect of Compound 5 and 7 on the liver to body weight ratio.

Unlike the reference compound (Elafibranor), both test compounds (Compounds 5 and 7) did not show any hepatomegaly and increase in liver to body weight ratio as shown in FIG. 3

In conclusion, the tested compounds lead to significant improvement in liver chemistry and histological activity of NASH. The therapeutic profile of Compounds 5 and 7 suggests that they have a potential for the treatment of human NASH. All treated animals presented body weight gain and had no clinical signs of toxicity or side effects.

Example 16: Effect of Compound 7 in the Treatment of Bleomycin-Induced IPF

IPF Induction

Timed pregnant mice (n=30) were selected for the study. The delivered pups were subcutaneously injected on the post-natal day 2 (PND-2) with 1.5 U/kg of Bleomycin (intra-tracheal) and were allowed to remain with the mother until they reached the weanling age. After weanling, the male pups were selected and fed with 60% kcal fat diet (Research Diet-D12492) for the next week. All the animals were observed twice daily for clinical signs.

Study Procedure

Mice were orally dosed with vehicle, test compounds and reference compound (Pirfenidone) twice daily morning (9.00 AM) and evening before the start of dark cycle (6:00 PM) from day 0 to 14.

Animal body weight measurements were made daily for the complete duration of the experiment.

Animals were dosed for 14 days with the test and reference compounds.

Lung hydroxyproline level was estimated before the treatment start and on the termination day 14. Total cell count and differential leukocyte count in BALF were measured before the treatment start and on day 28.

Histopathology analysis in the form of H&E Ashcroft score was performed for the lung tissues.

Sample Analysis

IPF Scoring: H&E Staining

All the H&E stained tissue sections were examined by light microscopy. As per the below grading system (Kleiner et al., 2005) in 200× objective lens, IPF scoring was carried out.

Collagen Proportion Area (% CPA) Measurement: Masson's Trichrome Staining All the Masson's trichrome stained tissue sections were examined by light microscopy in 100× objective lens. Randomly selected five fields (approx 684.85 μm×917.11m per field) from each lung were subjected to collagen proportion area measurement by using Image Pro Premier 9.1 software. The percentage of collagen proportion area was calculated by dividing collagen tissue area by total tissue area.

Figure 4:
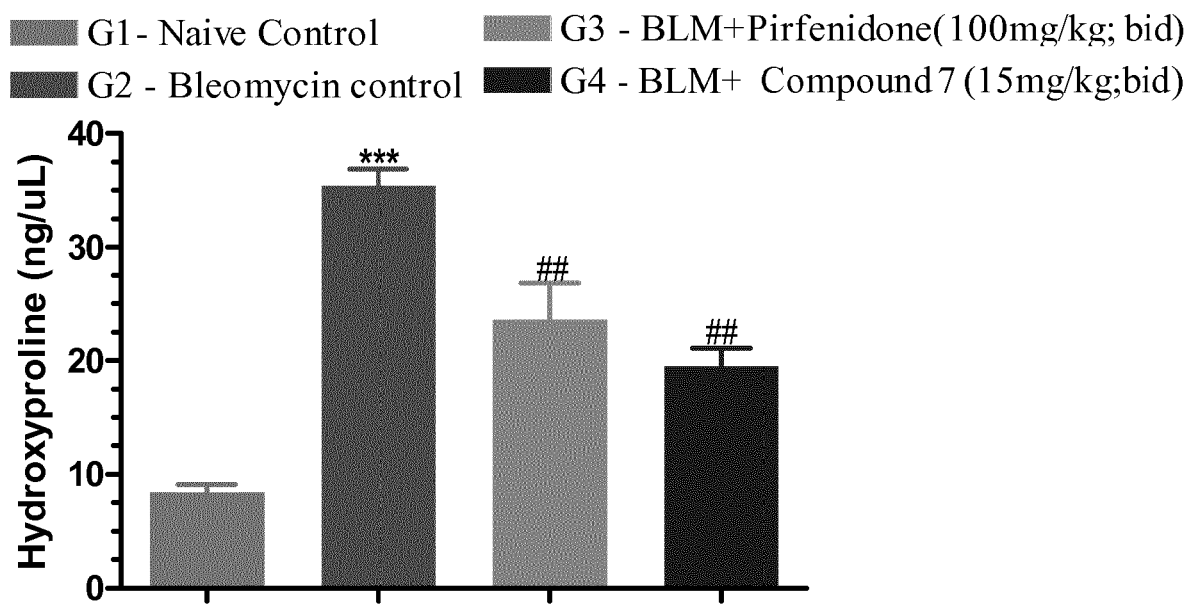
FIG. 4. Effect of Compound 7 on lung hydroxyproline levels in the treatment of bleomycin-induced IPF.

The effect of Compound 7 on lung hydroxyproline levels is shown in FIG. 4.

Lung hydroxyproline levels were significantly increased in Bleomycin control in comparison to Naïve control. The study clearly demonstrated that Compound 7 at the 15 mg/kg dose significantly reduced lung hydroxyproline levels and that the reduction was higher than for 100 mg/kg Pirfenidone.

Figure 5A:
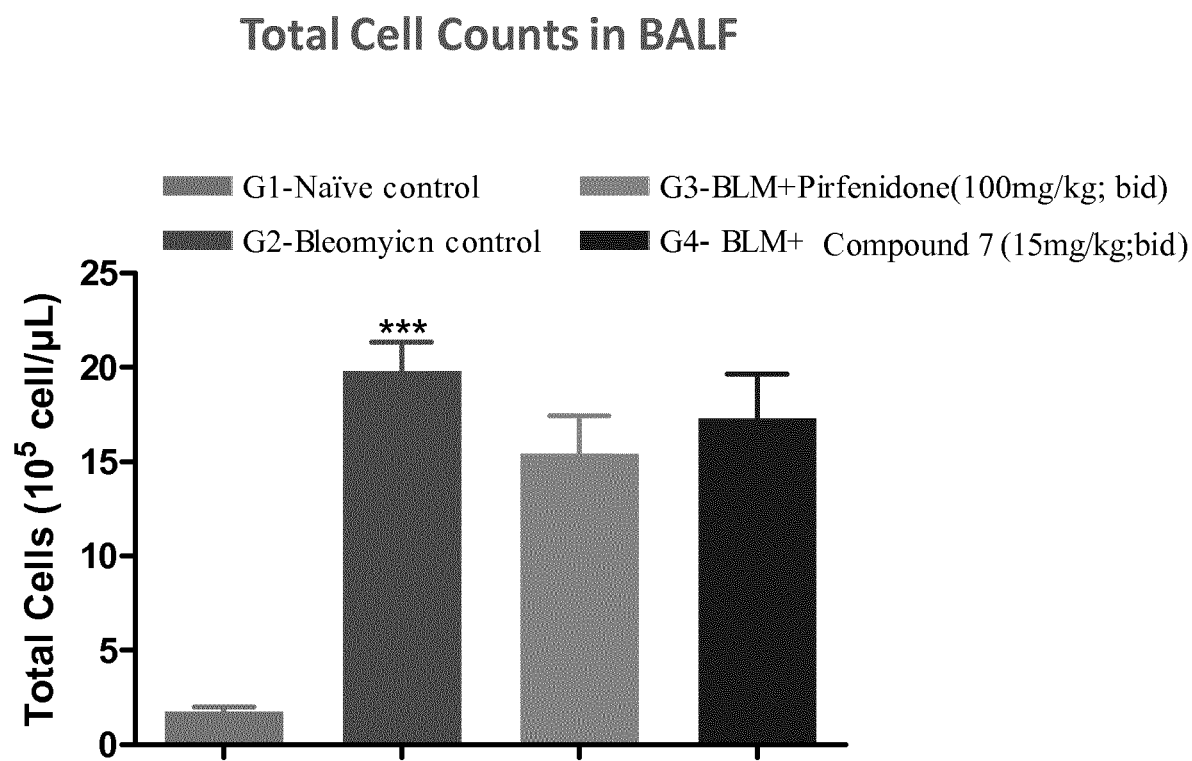
FIG. 5A. Total Cell Counts in BALF.
Figure 5B:
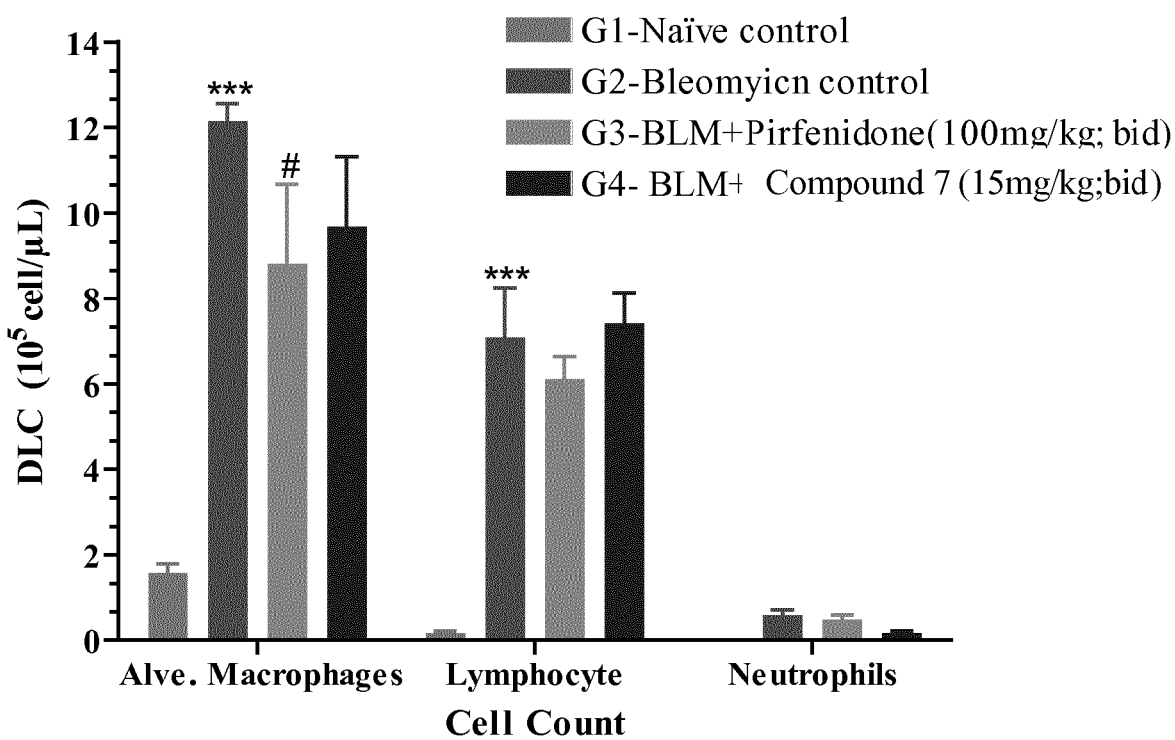
FIG. 5B. Differential Leukocyte Counts in BALF.

In BALF, total and Differential leukocyte (macrophage and lymphocyte) counts were significantly increased in Bleomycin control group. BALF macrophage counts were reduced with Compound 7 (p>0.05) and Pirfenidone (p<0.05) treatment as compared with Bleomycin control as shown in FIGS. 5A and 5B.

Figure 6A:
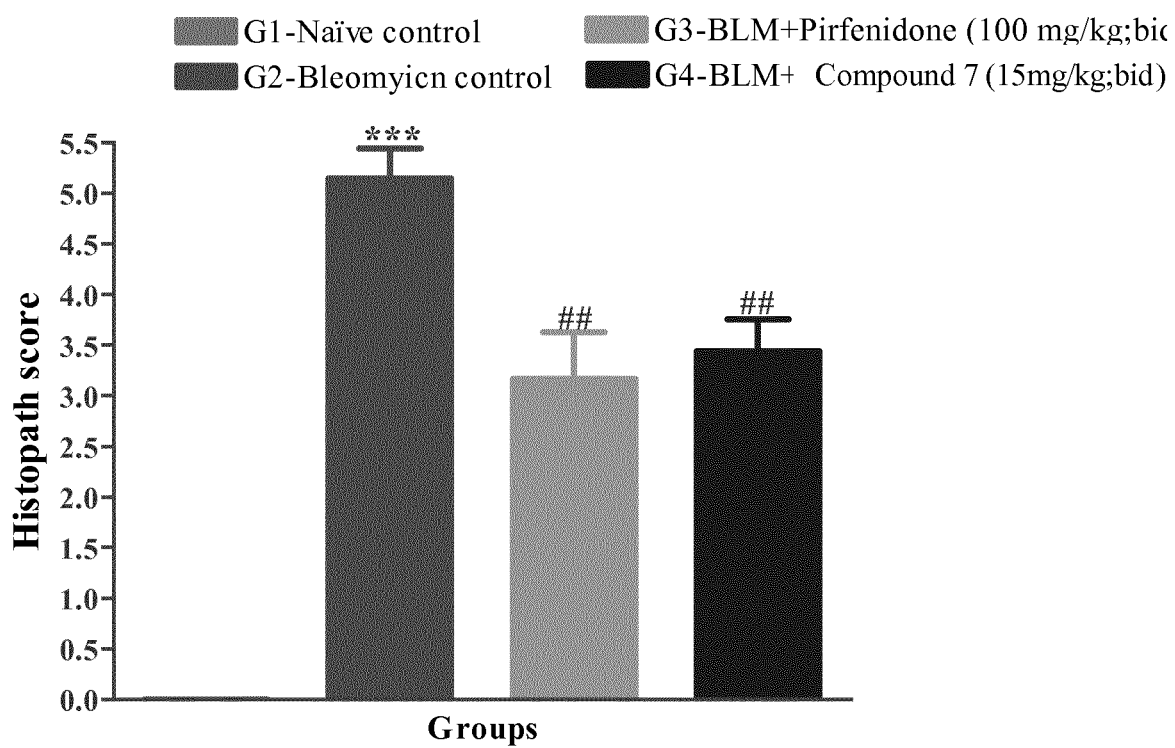
FIG. 6A. H&E Ashcroft Score.
Figure 6B:
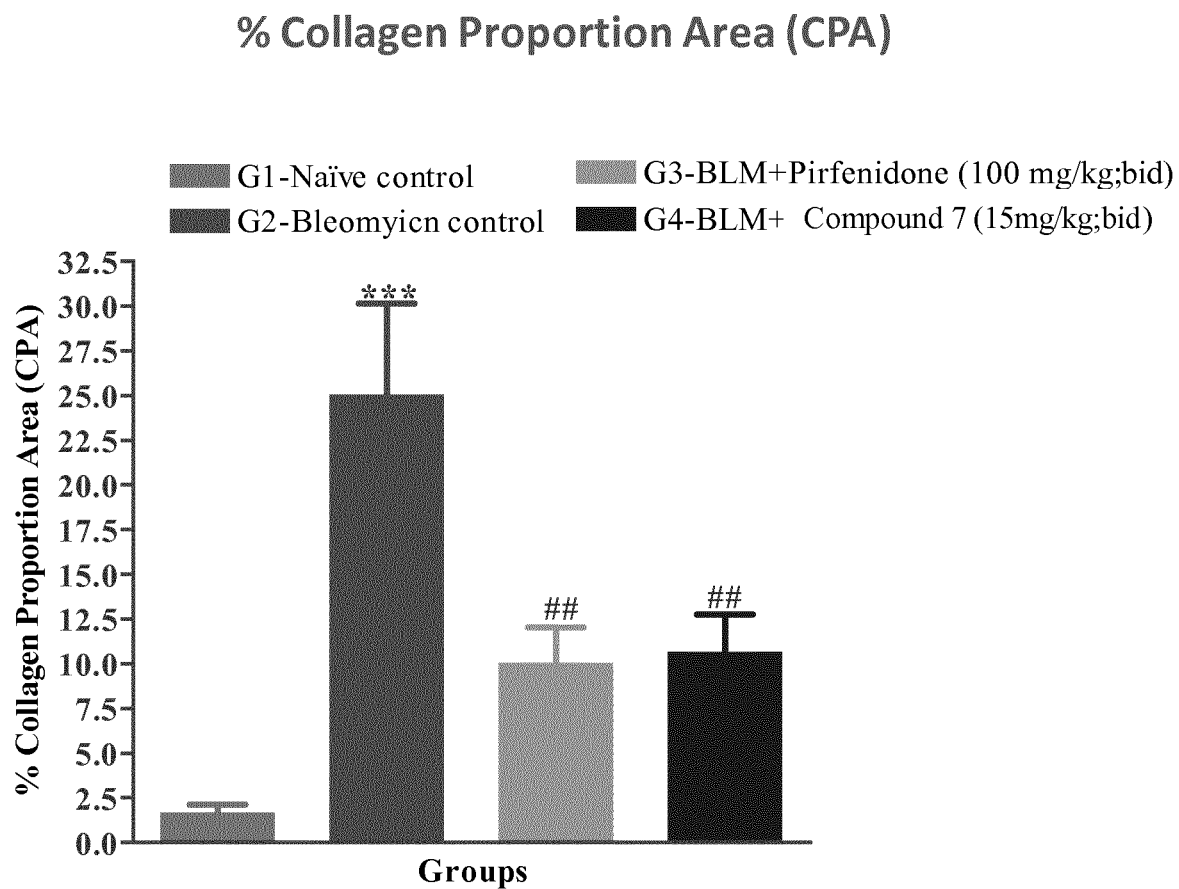
FIG. 6B. % Collagen Proportion Area (CPA).

Fibrosis score and % CPA were significantly increased in Bleomycin control lungs in comparison to Naïve control. Compound 7 (p<0.05) and Pirfenidone (p<0.05) treated lung samples exhibited a significant reduction in both fibrosis score and % CPA in comparison with Bleomycin control as shown in FIGS. 6A and 6B. The data is in line with hydroxyproline results.

In conclusion, the tested compound leads to significant improvement in lung chemistry and histological activity of IPF. The therapeutic profile of Compound 7 suggests that it has a potential for the treatment of human IPF. All treated animals presented body weight gain compared to Bleomycin control and had no clinical signs of toxicity or side effects.

The invention claimed is:

1. A compound of Formula Ia and pharmaceutically acceptable salts thereof:

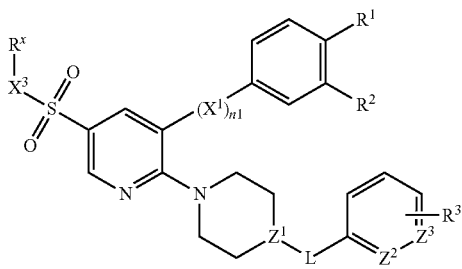

Formula Ia wherein:
(i) R' is selected from the group consisting of $C_{1-4}$ alkyl-$Y^1$—, $C_{2-4}$ alkenyl-$Y^1$—, $C_{2-4}$ alkynyl-$Y^1$—$C_{1-4}$ alkyl-$Y^1$— substituted with halo, $C_{2-4}$ alkenyl-$Y^1$— substituted with halo, $C_{2-4}$ alkynyl-$Y^1$ substituted with halo, HO—$C_{1-4}$ alkanediyl-$Y^1$—, HO—$C_{2-4}$ alkenediyl-$Y^1$—, HO—$C_{2-4}$ alkynediyl-$Y^1$—, HO—$C_{1-4}$ alkanediyl-, HO—$C_{2-4}$ alkenediyl-, HO—$C_{2-4}$ alkynediyl-, $C_{1-4}$ alkyl-$C_{2-4}$ alkenyl-, $C_{2-4}$ alkynyl-$C_{1-4}$ alkyl substituted with halo, $C_{2-4}$ alkenyl-substituted with halo, $C_{2-4}$ alkynyl-substituted with halo, and halogen and $R^2$ is hydrogen; or
(ii) $R^1$ together with $R^2$ forms an aromatic, heteroaromatic, cyclic or heterocyclic five- or six-membered ring optionally substituted with one or two substituents selected from the group consisting of $C_{1-4}$ alkyl-$Y^1$— $C_{2-4}$ alkenyl-$Y^1$— $C_{2-4}$ alkynyl-$Y^1$— $C_{1-4}$ alkyl-$Y^1$— substituted with halo, $C_{2-4}$ alkenyl-$Y^1$— substituted with halo, $C_{2-4}$ alkynyl-$Y^1$ substituted with halo, HO—$C_{1-4}$ alkanediyl-, HO—$C_{2-4}$ alkenediyl-, HO—$C_{2-4}$ alkynediyl-, $C_{1-4}$ alkyl-$C_{2-4}$ alkenyl-, $C_{2-4}$ alkynyl- and halogen;

$Y^1$ is selected from the group consisting of O, S, NH, C(O), C(O)O, C(O)NH, O(CO) and NHC(O);
$X^1$ is NH, O, or $CH_2$;
n1 is 0 or 1;
$X^3$ is absent or $NR^y$;
$R^x$ and $R^y$ are independently $C_{1-4}$ alkyl, $C_{2-4}$ alkenyl, $C_{2-4}$ alkynyl, or H;
L is O, S, S(O), $S(O)_2$, NH, C(O), or $CH_2$;

$Z^1$, $Z^2$, and $Z^3$ are independently selected from N and CH; and $R^3$ is selected from the group consisting of H, halo, $C(O)NR^{2a}R^{2b}$, $C(O)OR^{2a}$, $OR^{2a}$, $NR^{2a}R^{2b}$, $OC(O)R^{2a}$, $NR^{2a}C(O)R^{2b}$, $C_{1-4}$ alkyl optionally substituted with one or more halo, $C_{2-4}$ alkenyl optionally substituted with one or more halo, and $C_{2-4}$ alkynyl optionally substituted with one or more halo, wherein $R^{2a}$ and $R^{2b}$ are independently selected from the group consisting of H, $C_{1-4}$ alkyl, $C_{2-4}$ alkenyl, and $C_{2-4}$ alkynyl.

2. The compound according to claim 1, wherein $Y^1$ is selected from the group consisting of O, S, NH, C(O), and C(O)NH.

3. The compound according to claim 1, wherein $X^1$ is NH or O, and n1 is 1.

4. The compound according to claim 1, wherein $X^3$ is $NR^y$.

5. The compound according to claim 1, wherein $R^x$ and $R^y$ are independently $C_{1-4}$ alkyl.

6. The compound according to claim 5, wherein $R^x$ and $R^y$ are methyl.

7. The compound according to claim 1, wherein L is O.

8. The compound according to claim 1, wherein $Z^1$ and $Z^3$ are CH.

9. The compound according to claim 1, wherein $R^3$ is selected from the group consisting of H, halo, and $C(O)NH_2$.

10. The compound according to claim 9, wherein $R^3$ is selected from the group consisting of Cl and $C(O)NH_2$.

11. The compound according to claim 1, which is selected from the group consisting of:

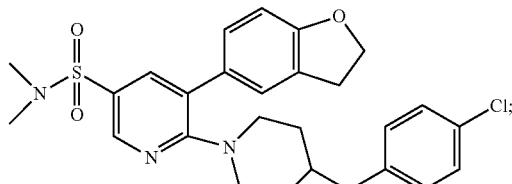

(1)

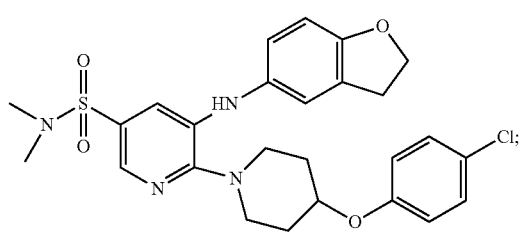

(2)

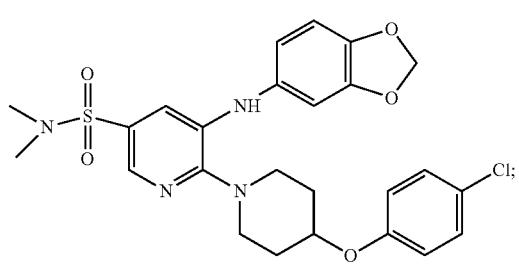

(3)

12. A pharmaceutical composition comprising a compound according to claim 1 and a pharmaceutically acceptable excipient or carrier.

13. A method for treating non-alcoholic steatohepatitis (NASH) or idiopathic pulmonary fibrosis (IPF), comprising administering the pharmaceutical composition of claim 12 to a subject in need thereof.

14. The compound of claim 1, wherein $C_{1-4}$ alkyl-$Y^1$— is substituted with fluoro.

15. The compound of claim 1, wherein $R^x$ and $R^y$ are independently H or $CH_3$.

* * * * *

UNITED STATES PATENT AND TRADEMARK OFFICE
CERTIFICATE OF CORRECTION

PATENT NO. : 12,071,431 B2
APPLICATION NO. : 17/293877
DATED : August 27, 2024
INVENTOR(S) : Miguel Vega et al.

It is certified that error appears in the above-identified patent and that said Letters Patent is hereby corrected as shown below:

In the Claims

Column 27, Claim 1, Line 39:
"R'"
Should read:
--$R^1$--.

Column 27, Claim 1, Line 40:
"$C_{2-4}$ alkynyl-$Y^1$-"
Should read:
--$C_{2-4}$ alkynyl-$Y^1$-,--.

Column 27, Claim 1, Line 46:
"$C_{2-4}$ alkynyl-"
Should read:
--$C_{2-4}$ alkynyl-,--.

Column 27, Claim 1, Line 53:
"$C_{1-4}$ alkyl-$Y^1$-"
Should read:
--$C_{1-4}$ alkyl- $Y^1$-,--.

Column 27, Claim 1, Line 54:
"$C_{2-4}$ alkenyl- $Y^1$-"
Should read:
--$C_{2-4}$ alkenyl- $Y^1$-,--.

Signed and Sealed this
Fifteenth Day of July, 2025

Coke Morgan Stewart
*Acting Director of the United States Patent and Trademark Office*

Column 27, Claim 1, Line 54:
"$C_{2-4}$ alkynyl- $Y^1$-"
Should read:
--$C_{2-4}$ alkynyl- $Y^1$-,--.
Column 29, Claim 11, Structure (8):
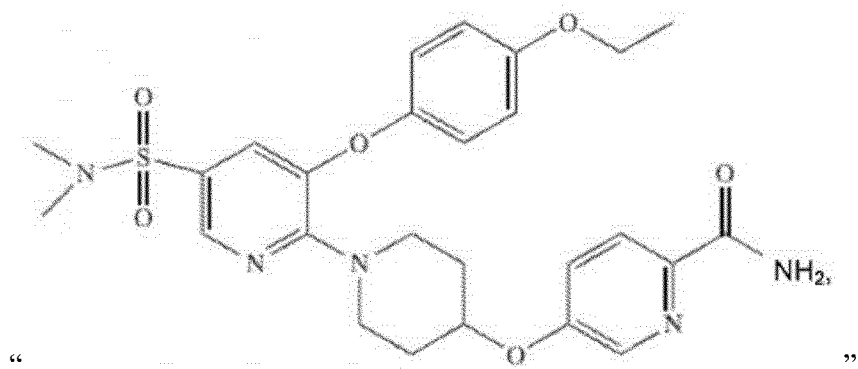
"
Should read:
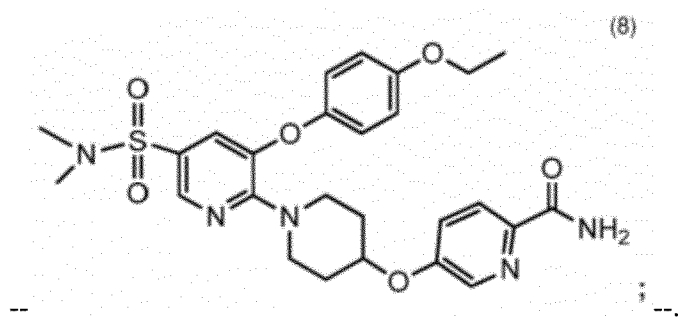
--     ;--.
Column 30, Claim 11, Structure (9):
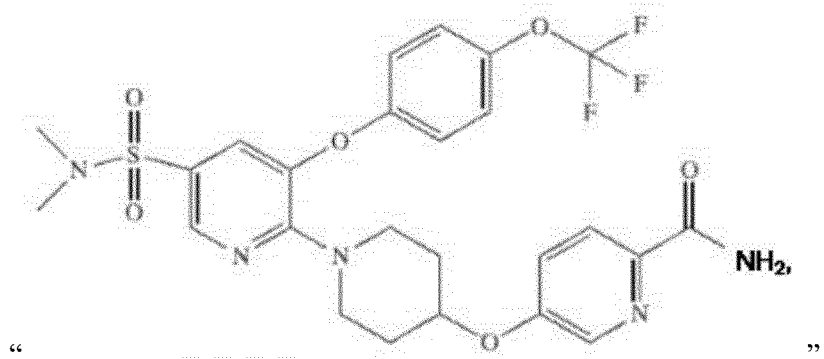
"                                                              "

Should read:
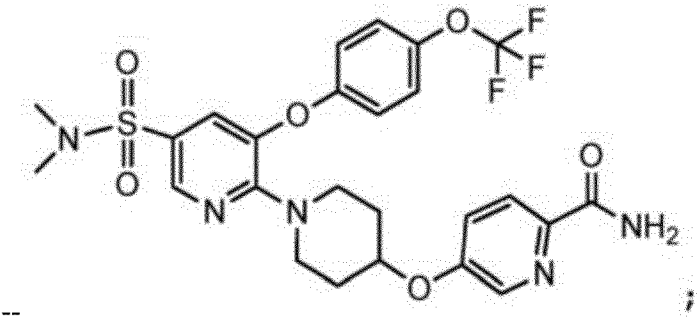
-- ; --.
Column 30, Claim 11, Structure (10):
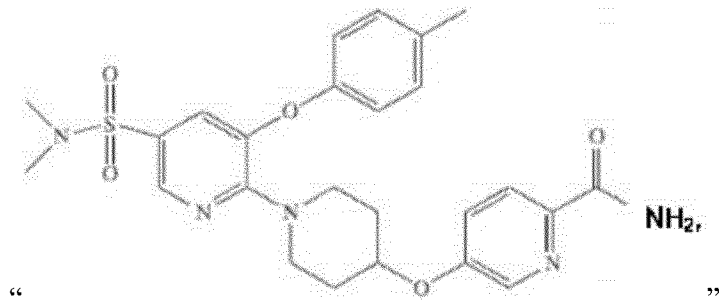
" "
Should read:
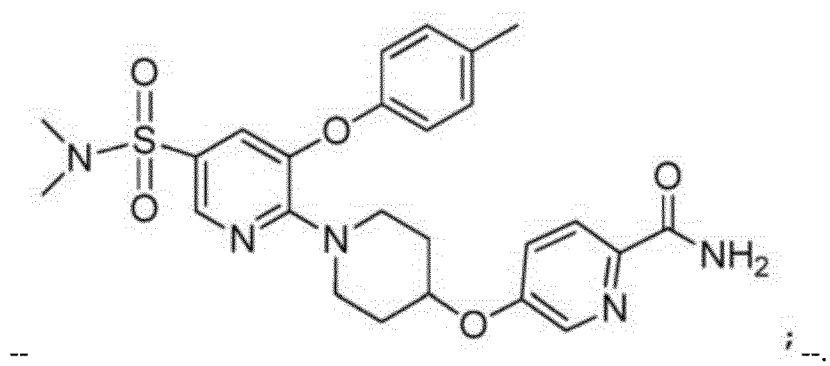
-- ; --.

CERTIFICATE OF CORRECTION (continued)
U.S. Pat. No. 12,071,431 B2

Column 30, Claim 11, Structure (11):

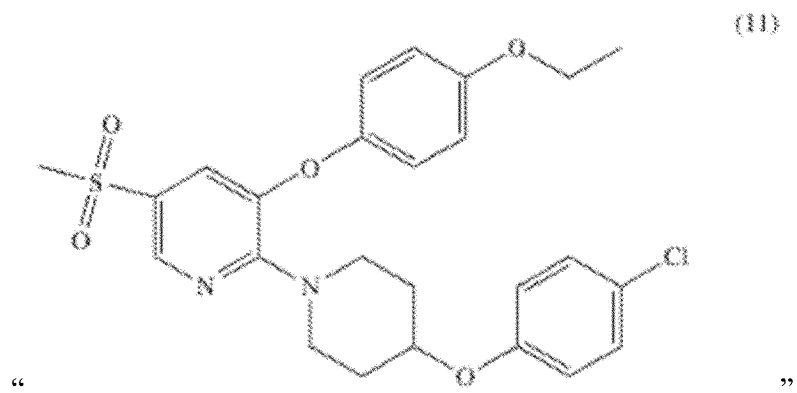

" "

Should read:

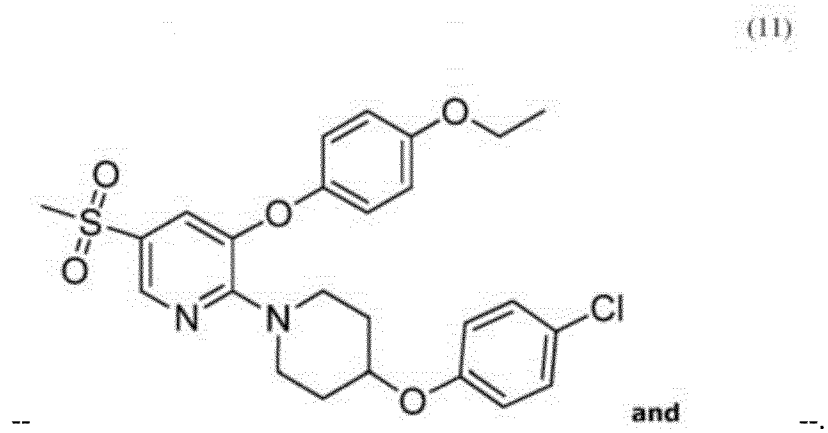

-- and --.